US012564580B2

(12) United States Patent
Dikalov et al.

(10) Patent No.: US 12,564,580 B2
(45) Date of Patent: Mar. 3, 2026

(54) MITOCHONDRIA-TARGETED ISOKETAL/ISOLEVUGLANDIN SCAVENGERS AND USES THEREOF

(71) Applicant: Vanderbilt University, Nashville, TN (US)

(72) Inventors: Sergey I Dikalov, Nashville, TN (US); Venkataraman Amarnath, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 733 days.

(21) Appl. No.: 17/795,861

(22) PCT Filed: Jan. 27, 2021

(86) PCT No.: PCT/US2021/015322
§ 371 (c)(1),
(2) Date: Jul. 27, 2022

(87) PCT Pub. No.: WO2021/154877
PCT Pub. Date: Aug. 5, 2021

(65) Prior Publication Data

US 2023/0098649 A1 Mar. 30, 2023

Related U.S. Application Data

(60) Provisional application No. 62/966,478, filed on Jan. 27, 2020.

(51) Int. Cl.
*A61K 31/4425* (2006.01)
*A61K 31/137* (2006.01)
*A61P 31/00* (2006.01)

(52) U.S. Cl.
CPC ........ *A61K 31/4425* (2013.01); *A61K 31/137* (2013.01); *A61P 31/00* (2018.01)

(58) Field of Classification Search
CPC .... A61K 31/4425; A61K 31/137; A61P 31/00
See application file for complete search history.

(56) References Cited

U.S. PATENT DOCUMENTS

2008/0275005 A1 11/2008 Murphy et al.
2014/0256774 A1 * 9/2014 Roberts .................... A61P 9/12
514/351
2016/0289252 A1 10/2016 Murphy et al.

FOREIGN PATENT DOCUMENTS

WO WO 2018/093936 A1 5/2018
WO WO 2020/154724 A1 7/2020

OTHER PUBLICATIONS

Dikalova, et al., Mitochondrial Isolevuglandins Contribute to Vascular Oxidative Stress and Mitochondria-Targeted. Scavenger of Isolevuglandins Reduces Mitochondrial Dysfunction and Hypertension; Hypertension; 2023, pp. 1980-1991.
Mayorov et al. "Targeting of reactive Isolevuglandins in mitochondrial dysfunction and inflammation" Redox Biology. Aug. 14, 2019 (Aug. 14, 2019) vol. 26, p. 1-9.
"Pubchem CID 144100440" Create Date: Dec. 7, 2019 (Dec. 7, 2019); p. 2.
Zielonka, et al., Mitochondria-Targeted Triphenyiphosphonium-Based Compounds: Syntheses, Mechanisms of Action, and Therapeutic and Diagnostic Applications; Chem Rev. Aug. 9, 2017; 117(15): 10043-10120

* cited by examiner

*Primary Examiner* — Timothy R Rozof
(74) *Attorney, Agent, or Firm* — Stites & Harbison PLLC; Richard S. Myers, Jr.

(57) ABSTRACT

The use of novel 2-hydroxybenzylamine derivatives as scavengers of isolevuglandins.

10 Claims, 14 Drawing Sheets

A: Synthesis of Mitochondria Targeted mito2HOBA mito2HOBA

Reagents: (a) $Br(CH_2)_4Br$, $Cs_2CO_3$, $CH_3CN$, 80 °C, 50%; (b) $P(C_6H_5)_3$, toluene, reflux, 60%; (c) $NH_2OH.HCl$, $CH_3CO_2Na$, $C_2H_5OH$, 95%; (d) Zn, $CH_3CO_2H$, 60 °C 75%.

B: mito2HOBA is effective scavenger of IsoLG

Second-order rate constants (1/M*s) for reaction with 4-oxopentanal to form pyrrole

MITOCHONDRIA-TARGETED ISOKETAL/ISOLEVUGLANDIN SCAVENGERS AND USES THEREOF

RELATED APPLICATIONS

This application claims priority from International Patent Application No. PCT/US2021/015322, filed Jan. 27, 2021, which claims benefit to U.S. Provisional Application Ser. No. 62/966,478 filed Jan. 27, 2020, the entire disclosures of which are incorporated herein by this reference.

GOVERNMENT SUPPORT

This invention was made with government support under Grant nos. HL124116, HL129941, and HL144943, awarded by the National Institutes of Health. The government has certain rights in this invention.

BACKGROUND AND SUMMARY OF THE INVENTION

The present application relates to novel compounds and compositions, and uses thereof. The compounds of the present invention have been found to be useful in the treatment of diseases and conditions such as inflammation, sepsis, mitochondrial dysfunction, oxidative stress, and hypertension.

Inflammation is a major cause of morbidity and mortality in Western societies. Despite use of multiple drugs, both chronic and acute inflammation still represent major health burdens. Inflammation produces highly reactive dicarbonyl lipid peroxidation products such as isolevuglandins which covalently modify and cross-link proteins via lysine residues. Mitochondrial dysfunction has also been associated with inflammation.

The present inventors discovered that inflammation-induced isolevuglandins contribute to mitochondrial dysfunction and mortality. The present inventors have (a) investigated the mitochondrial dysfunction in response to synthetic 15-$E_2$-isolevuglandin (IsoLG) and its adducts; (b) developed novel mitochondria-targeted scavengers of isolevuglandins, including by conjugating 2-hydroxybenzylamine to the lipophilic cation triphenylphosphonium, (4-(4-aminomethyl)-3-hydroxyphenoxy)butyl)-triphenylphosphonium (mito2HOBA); (c) discovered that the compounds of the present invention, including mito2HOBA protect from mitochondrial dysfunction and mortality using a lipopolysaccharide model of inflammation.

Acute exposure to either IsoLG or IsoLG adducts with lysine, ethanolamine or phosphatidylethanolamine inhibits mitochondrial respiration and attenuates Complex I activity. Complex II function was much more resistant to IsoLG. The present inventors confirmed that compounds of the present invention, including mito2HOBA, markedly accumulates in isolated mitochondria and it is highly reactive with IsoLGs.

To test the role of mitochondrial IsoLGs, the present inventors studied the therapeutic potential of compounds of the present invention in lipopolysaccharide mouse model of sepsis. For example, mito2HOBA supplementation in drinking water (0.1 g/L) to lipopolysaccharide treated mice increased survival by 3-fold, improved complex I-mediated respiration, and histopathological analyses supported mito2HOBA—mediated protection of renal cortex from cell injury. These data support the role of mitochondrial IsoLG in mitochondrial dysfunction and inflammation. Thus, the present inventors were able to confirm that reducing mitochondrial IsoLGs is a therapeutic target in inflammation and conditions associated with mitochondrial oxidative stress and dysfunction.

Thus, aspects of the present invention include isolevuglandins and their adducts inhibiting mitochondrial respiration and attenuating Complex I activity; compounds of the present invention, including 2-Hydroxybenzylamine conjugated to triphenylphosphonium, mito2HOBA, accumulates in mitochondria; mito2HOBA in drinking water improves complex I-mediated respiration in LPS model of sepsis; and mitochondria-targeted scavenger of isolevuglandins mito2HOBA reduces mortality in LPS models.

Likewise, hypertension remains a major health problem in Western Societies, and blood pressure is poorly controlled in a third of patients despite use of multiple drugs. Mitochondrial dysfunction contributes to hypertension and mitochondria-targeted agents can potentially improve treatment of hypertension. The present inventors show that mitochondrial oxidative stress produces reactive dicarbonyl lipid peroxidation products isolevuglandins (isoLGs) and that scavenging of mitochondrial isoLG improves vascular function and reduces hypertension. To test this hypothesis, we have studied the accumulation of mitochondrial isoLGs-protein adducts in patients with essential hypertension and angiotensin II model of hypertension using mass spectrometry and Western blot analysis. The therapeutic potential of targeting mitochondrial isoLG was tested by the novel mitochondria-targeted isoLG scavenger, mito2HOBA. Mitochondrial isoLGs in arterioles from hypertensive patients were 250% greater than in arterioles from normotensive subjects, and ex vivo mito2HOBA treatment of arterioles from hypertensive subjects increased deacetylation of a key mitochondrial antioxidant, superoxide dismutase 2 (SOD2). In human aortic endothelial cells stimulated with angiotensin II plus TNFα, mito2HOBA reduced mitochondrial superoxide and cardiolipin oxidation, a specific marker of mitochondrial oxidative stress. In angiotensin II-infused mice, mito2HOBA diminished mitochondrial isoLGs-protein adducts, raised Sirt3 mitochondrial deacetylase activity, reduced vascular superoxide, increased endothelial nitric oxide, improved endothelium-dependent relaxation, and attenuated hypertension. Mito2HOBA preserved mitochondrial respiration, protected ATP production, and reduced mitochondrial permeability pore opening in angiotensin II-infused mice. These data support the role of mitochondrial isoLGs in endothelial dysfunction and hypertension. The present inventors have discovered that scavenging of mitochondrial isoLGs has a therapeutic benefit in treatment of vascular dysfunction and hypertension.

By recent guidelines, almost one-half of adults have hypertension, and an estimated 1.4 billion people have hypertension worldwide. This disease represents a major risk factor for stroke, myocardial infarction, and heart failure. Despite treatment with multiple drugs, a third of hypertensive patients remain hypertensive, likely due to the mechanisms that are not affected by current treatments. There is a long felt need for new classes of antihypertensive agents that can improve treatment of hypertension. Hypertension is a multifactorial disorder and oxidative stress is increased in multiple organs in hypertension. Oxidative stress contributes to hypertension by increasing sympathetic outflow, promoting kidney dysfunction, and increasing systemic vascular resistance. Meanwhile, common antioxidants, like ascorbate and vitamin E, are ineffective in the treatment of cardiovascular diseases and hypertension, and in some studies have worsen the outcome. Intrinsic enzymatic antioxidants are much more effective against oxidative stress compared with low molecular weight antioxidants, but these intrinsic antioxidants can be inactivated in hypertension. Essential hypertension is associated with inactivation of a key mitochondrial antioxidant, superoxide dismutase 2 (SOD2), by acetylation of lysine residues at the catalytic center due to reduced activity of mitochondrial deacetylase sirtuin 3 (Sirt3), however the precise mechanism of Sirt3 inactivation and molecular consequences of SOD2 inhibition are not known.

One potential mechanism involves lipid peroxidation, particularly the formation of mitochondrial isolevuglandins (isoLGs). IsoLGs are highly reactive and harmful dicarbonyl lipid peroxidation products. They are produced by peroxidation of arachidonic acid by oxidizing species such as the protonated form of superoxide, the hydroperoxyl radical. IsoLGs rapidly adduct to primary amines such as protein lysine residues promoting cell dysfunction. In dendritic cells, isoLGs promote modification of self-proteins, which can act as neoantigens driving an adaptive immune response. Treatment with the isoLG scavenger, 2-hydroxybenzylamine (2HOBA), reduces dendritic and T cell activation and attenuates angiotensin II- and DOCA-salt induced hypertension. Of note, 2HOBA is not an antioxidant but it reduces superoxide production in dendritic cells by scavenging the reactive isoLGs and decreasing the dendritic cells activation. The specific sources and the targets of isoLGs, however, remain elusive. The pathophysiological role of isoLGs is not limited to dendritic cells as isoLGs can be produced in vascular tissue, endothelial, epithelial, and other cells. Hypertension is associated with mitochondrial oxidative stress, and the mitochondria can be a potential source of isoLGs, but the role of mitochondrial isoLGs in hypertension has not been studied. The present inventors show that mitochondrial isoLGs may contribute to Sirt3 inactivation and mitochondrial dysfunction in hypertension.

Treatment of isolated mitochondria with bolus isoLGs disrupts mitochondrial respiration and promotes mitochondrial permeability transition pore (mPTP) opening. To study the specific role of intra-mitochondrial isoLGs in vivo, the present inventors have developed the mitochondria-targeted isoLG scavenger mito2HOBA by conjugating 2HOBA to the lipophilic cation triphenylphosphonium. Mito2HOBA does not scavenge the reactive oxygen species. Without being bound by theory or mechanism, it can potentially react with different gamma-ketoaldehydes, but it is particularly reactive with isoLGs. Mito2HOBA accumulates in mitochondria and mito2HOBA supplementation in a lipopolysaccharide mouse model of sepsis increases animal survival by 3-fold, increases complex I-mediated respiration, and prevents renal cortical injury supporting the role of mitochondrial isoLGs in mitochondrial dysfunction.

Mitochondrial dysfunction contributes to the pathogenesis of hypertension and cardiovascular disease; however, despite the central role of mitochondria in human health and disease, there are no approved drugs that directly target mitochondria. Mitochondrial dysfunction is characterized by reduced ATP levels and increased oxidative stress leading to cell dysfunction and apoptosis. Opening of the mitochondrial permeability transition pore (mPTP) plays a key role in mitochondrial dysfunction and end-organ-damage in hypertension. The present inventors discovered that depletion or inhibition of Cyclophilin D (CypD), a regulatory subunit of mPTP opening, improves vascular function and attenuates hypertension. Interestingly, CypD acetylation at lysine 166 promotes mPTP opening and mitochondrial Sirt3 deacetylates CypD-K166.

Sirt3 is key node in regulation of metabolic and antioxidant mitochondrial functions. Sirt3 depletion promotes endothelial dysfunction, vascular hypertrophy, vascular inflammation and end-organ damage. Clinical studies show that cardiovascular disease risk factors are associated with reduced Sirt3 level and activity. The present inventors discovered that Sirt3 impairment is a new convergent mechanism underlying the interplay of major cardiovascular risk factors. The present inventors show that mitochondrial isoLGs inactivate Sirt3, and scavenging of mitochondrial isoLGs protects Sirt3 activity, improves vascular function and reduces hypertension.

Abbreviations used herein include IsoLG, isolevuglandins (aka isoketals); PE, phosphatidylethanolamine; 15-$E_2$-IsoLG, 15-$E_2$ stereoisomer of isolevuglandins; 15-$E_2$-IsoLG-PE, adduct of PE with 15-$E_2$-IsoLG stereoisomer; 2HOBA, 2-hydroxybenzylamine; 4HOBA, non-scavenger analog of 2HOBA, 4-hydroxybenzylamine; mito2HOBA, conjugate of 2-hydroxybenzylamine to lipophilic cation triphenylphosphonium, (4-(4-aminomethyl)-3-hydroxyphenoxy)butyl)-triphenylphosphonium; mitoTEMPO, (2-(2,2,6,6-tetramethylpiperidin-1-oxyl-4-ylamino)-2-oxoethyl) triphenylphosphonium; mPTP, mitochondrial permeability transition pore; PUFA, polyunsaturated fatty acids; ROS, reactive oxygen species; LPS, Lipopolysaccharide; WT, wild-type C57BL/6J mice; SMP, submitochondrial particles.

DESCRIPTION OF THE INVENTION

Figure 1:
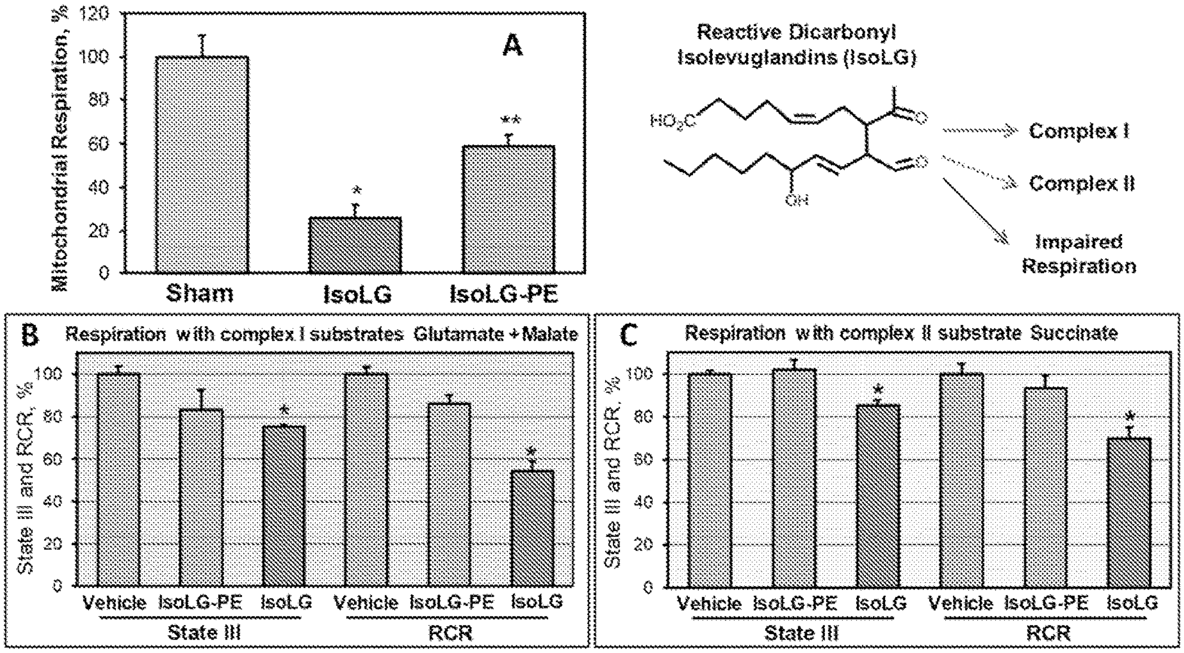
FIGS. 1A-1C show acute treatment with IsoLG or IsoLG-PE impairs mitochondrial respiration. (A) Intact mouse kidney mitochondria were incubated (5 min) with ethanol as vehicle (Sham), IsoLG (20 μM) or IsoLG-PE (20 μM) and then diluted with respiration buffer 20-fold prior to addition of Glutamate and Malate, ADP (50 μM) and measurements of oxygen consumption in State III. *P<0.001 vs Sham, **P<0.03 vs IsoLG. (B) Oxygen consumption in the presence of complex I substrates Glutamate+Malate and ADP (State III) and Respiratory Control Ratio (State III/State IV, %) in intact kidney mitochondria treated with vehicle, IsoLG (1.5 μM) or IsoLG-PE (1.5 μM) in the respiration chamber. (C) State III respiration and Respiratory Control Ratio (State III/State IV, %) in presence of complex II substrate Succinate and ADP following addition of vehicle, IsoLG (1.5 μM) or IsoLG-PE (1.5 μM) in the respiration chamber. Data are expressed as mean±STD (N=4-6). *P<0.01 vs Vehicle.

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or cannot occur, and that the description includes instances where said event or circumstance occurs and instances where it does not.

As used herein, the term "subject" refers to a target of administration. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed. As can be seen herein, there is overlap in the definition of treating and preventing.

As used herein, the term "diagnosed" means having been subjected to a physical examination by a person of skill, for example, a physician, and found to have a condition that can be diagnosed or treated by the compounds, compositions, or methods disclosed herein. As used herein, the phrase "identified to be in need of treatment for a disorder," or the like, refers to selection of a subject based upon need for treatment of the disorder. For example, a subject can be identified as having a need for treatment of a disorder (e.g., a disorder related to inflammation) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

The present invention relates to mitochondria-targeted derivatives of 2-hydroxybenzylamine that are scavengers of highly reactive lipid dicarbonyls derived from arachidonic acid and other polyunsaturated fatty acids, isolevuglandins (isoLG, also known as isoketals or gamma-ketoaldehydes), pharmaceutical compositions comprising such compounds, and methods of treating conditions involving mitochondrial dysfunction, oxidative stress, e.g., mitochondrial oxidative stress, hypertension, and sepsis.

In another embodiment of the present invention, a method is provided for treating, preventing, and ameliorating mitochondrial dysfunction in a subject, comprising administering an effective amount of a mitochondria-targeted scavenger of the present invention, or a pharmaceutically acceptable salt thereof.

In another embodiment of the present invention, a method is provided for treating, preventing, and ameliorating oxidative stress in a subject, comprising administering an effective amount of a compound of the present invention, or a pharmaceutically acceptable salt thereof.

In another embodiment of the present invention, a method is provided for treating, preventing, and ameliorating hypertension in a subject, comprising administering an effective amount of a compound of the present invention, or a pharmaceutically acceptable salt thereof.

In another embodiment of the present invention, a method is provided for treating, preventing, and ameliorating sepsis in a subject, comprising administering an effective amount of a compound of the present invention, or a pharmaceutically acceptable salt thereof.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

In one aspect, the invention relates to compounds, or pharmaceutically acceptable derivatives thereof, useful in the treatment of the indications described herein, including inflammation, hypertension, mitochondrial oxidative stress, and mitochondrial dysfunction. In general, it is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using. It is also understood that the disclosed compounds can all be employed as corresponding pharmaceutical compositions.

One embodiment of the present invention is a compound of the following formula:

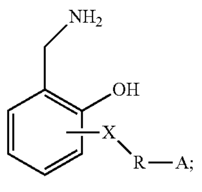

wherein:

X is a bond, alkyl, alkoxy, methoxy, —O—, or —$CH_2$—;

each R is independent and chosen from $C_1$ to $C_{12}$ substituted or unsubstituted alkyl; and A is

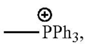, 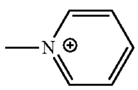, 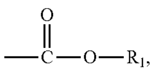,

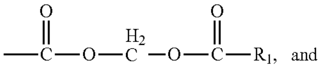, and

-continued

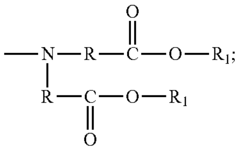

each $R_1$ is independent and chosen from $C_1$ to $C_{12}$ substituted or unsubstituted alkyl; and an optional counterion; and stereoisomers and pharmaceutical salts thereof.

Another embodiment of the present invention a compound of the following formula:

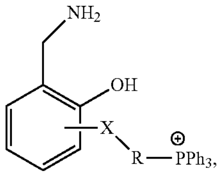

wherein:

X is a bond, alkyl, —O—, or —$CH_2$—; and

R is $C_1$ to $C_{12}$ substituted or unsubstituted alkyl; and stereoisomers and pharmaceutical salts thereof.

Another embodiment of the present invention is a compound of the following formula:

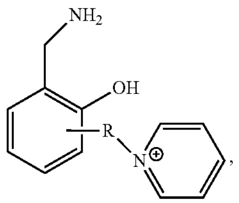

wherein

R is $C_1$ to $C_{12}$ substituted or unsubstituted alkyl; and stereoisomers and pharmaceutical salts thereof.

Another embodiment of the present invention is a compound of the following formula:

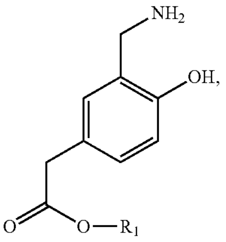

wherein $R_1$ is $C_1$ to $C_{12}$ substituted or unsubstituted alkyl; and stereoisomers and pharmaceutical salts thereof.

Another embodiment of the present invention is a compound of the following formula:

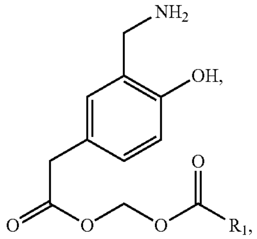

wherein $R_1$ is $C_1$ to $C_{12}$ substituted or unsubstituted alkyl; and stereoisomers and pharmaceutical salts thereof.

Another embodiment of the present invention is a compound of the following formula:

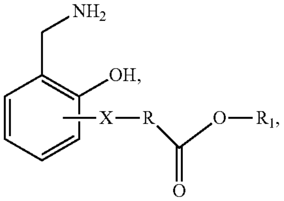

wherein

X is a bond, —O—, or —$CH_2$—;

R is $C_1$ to $C_{12}$ substituted or unsubstituted alkyl; and $R_1$ is $C_1$ to $C_{12}$ substituted or unsubstituted alkyl or acetoxymethyl; and stereoisomers and pharmaceutical salts thereof.

Another embodiment of the present invention is a compound of the following formula:

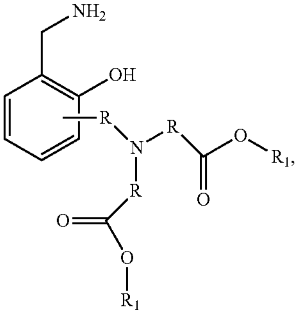

wherein each R is independent and chosen from $C_1$ to $C_{12}$ substituted or unsubstituted alkyl; and each $R_1$ is independent and chosen from $C_1$ to $C_{12}$ substituted or unsubstituted alkyl or acetoxymethyl; and stereoisomers and pharmaceutical salts thereof.

In another embodiment, the mitochondria-targeted scavenger is a compound of the following formula:

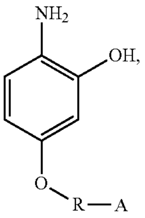

wherein

R is $C_1$ to $C_{12}$ substituted or unsubstituted alkyl; $R_2$ is selected from —P—$Ph_3$; or

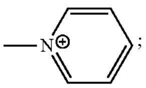

and stereoisomers and pharmaceutical salts thereof.

Another embodiment of the present invention is a compound of the following formula:

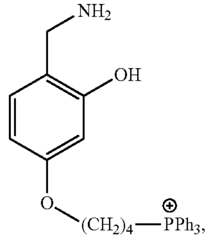

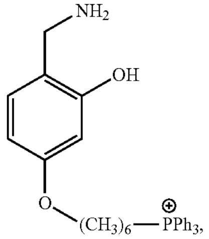

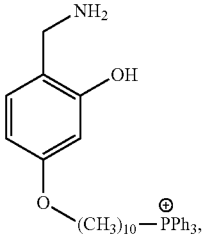

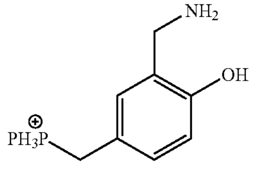

,

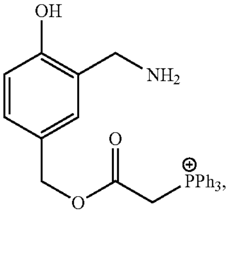

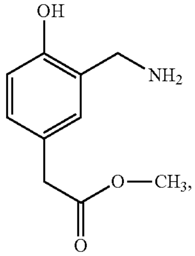

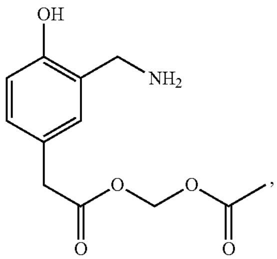

-continued

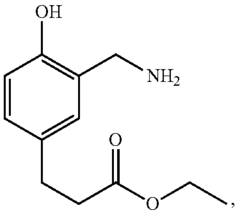

and

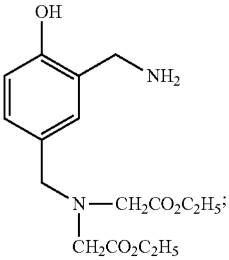

and pharmaceutically acceptable salts thereof.

Another embodiment of the present invention is a compound is of the following formula:

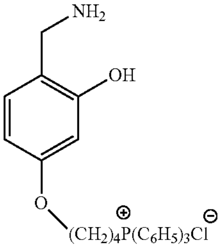

mito2HOBA

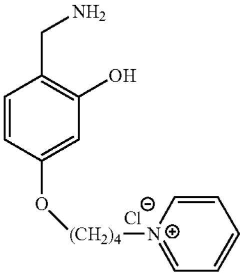

mito2HOBA-4N4

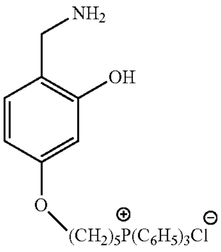

mito2HOBA-C6

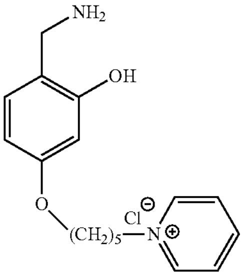

mito2HOBA-4N6

-continued

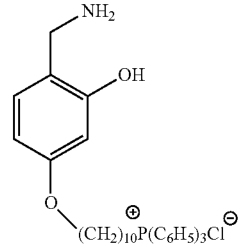

mito2HOBA-C10

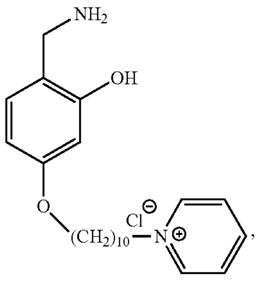
, mito2HOBA-4N10 and stereoisomers and pharmaceutical salts thereof.

General Schemes

Synthesis of mitochondria-targeted isoLG scavengers of the present invention is described below.

Synthetic Scheme for Ether Linkage

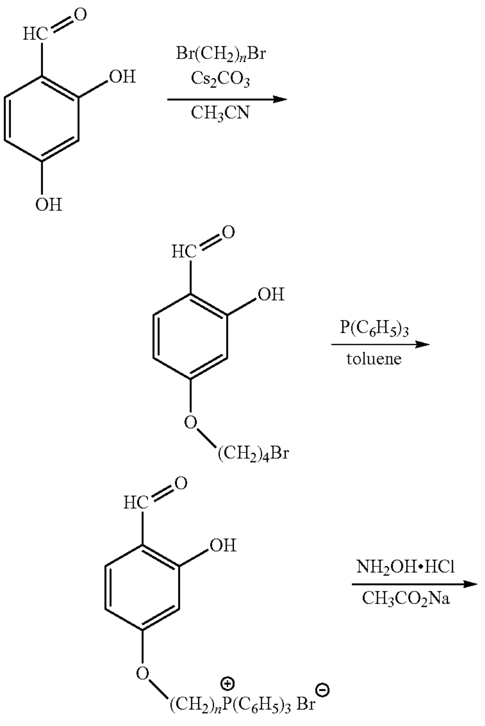

-continued

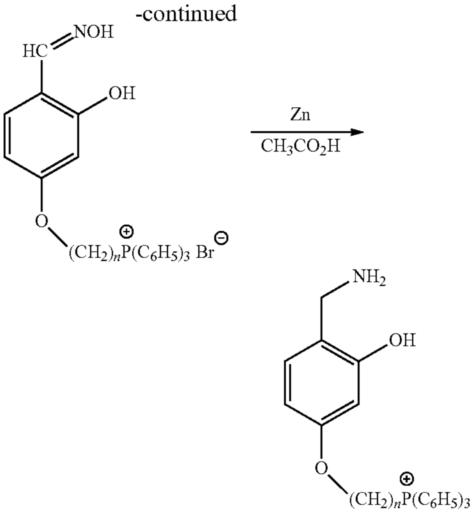

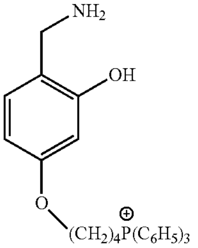

mito2HOBA-C4
(4-(4-(aminomethyl)-3-hydroxyphenoxy)butyl)triphenylphosphonium

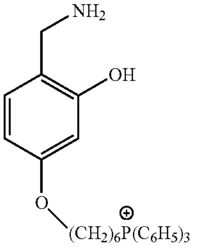

mito2HOBA-C6
(6-(4-(aminomethyl)-3-hydroxyphenoxy)hexyl)triphenylphosphonium

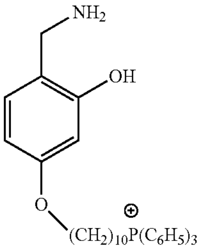

mito2HOBA-C10
(10-(4-(aminomethyl)-3-hydroxyphenoxy)decyl)triphenylphosphonium

Cesium carbonate (4.9 g, 15 mmol) was added to 2,4-dihydroxybenzaldehyde (4.2 g, 30 mmol) and 1,4-dibromobutane (6.6 g, 30 mmol) in acetonitrile (50 ml). The mixture was heated at 80° C. under argon for 5 h, cooled and added to 1 M phosphate buffer, pH 7 (30 ml), ice and $KH_2PO_4$ (2 g) with mixing. The solid was removed by filtration and the filtrate was extracted with ethyl acetate. Purification by column (silica, 9:1 hexane-ethyl acetate) yielded 4-(4-bromobutoxy)2-hydroxybenzaldehyde (4.1 g, 50%). It was mixed with triphenylphosphene (4.2 g) in toluene (75 ml) and refluxed under argon for 15 h. The pink solid was purified by flash chromatography (0-10% methanol in dichloromethane to get 4-(4-formyl-3-hydroxyphenoxy)butyl)triphenylphosphonium bromide (4.8 g, 60%). The aldehyde was converted to oxime by stirring with $NH_2OH \cdot HCl$ (0.63 g) and $CH_3CO_2Na$ (0.74 g) in ethanol (40 ml) for 1 h. The crude product was dissolved in acetic acid (40 ml) and treated with zinc powder (6 g). The reaction mixture was slowly heated in a water bath to 60° C., kept at that temperature for 20 m, cooled, and filtered. Acetic acid was removed and the residue was purified by column chromatography (silica; 5-20% 0.1 M ammonium acetate-acetonitrile). Other compounds are similarly prepared using appropriate dibromoalkanes.

Scheme for Methylene Linkage:

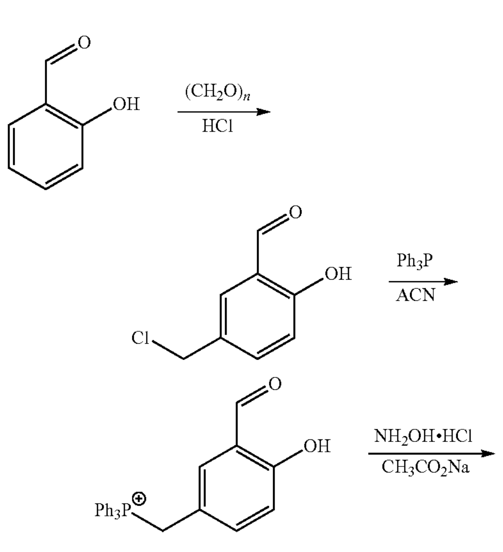

-continued

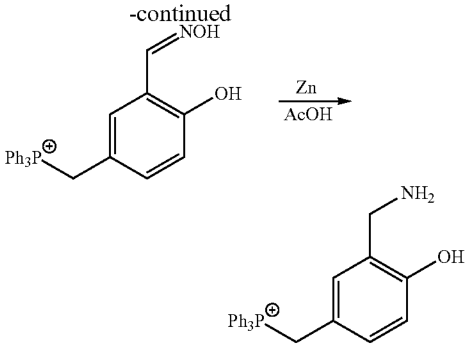

mito2HOBA-C1
(3-(aminomethyl)-4-hydroxybenzyl) triphenylphosphonium 5-(Chloromethyl)-2-hydroxybenzaldehyde (4.5 g) was refluxed with triphenylphosphine (5.75 g) in acetonitrile for 5 h. After cooling, the adduct was purified by column (silica; 0-15% methanol in dichloromethane). The aldehdye was converted to oxime, reduced with zinc in acetic acid, and purified as described for mito2HOBA-C4. The alkyl chain may be extended.

The original mitoSalicylamine analog was prepared as shown below:

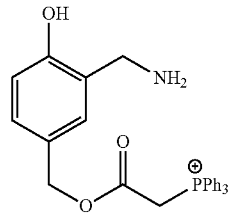

(2-((3-(aminomethyl)-4-hydroxybenzyl)oxy)-2-oxoethyl)triphenylphosphonium

Synthetic Scheme for Esters and Acids:

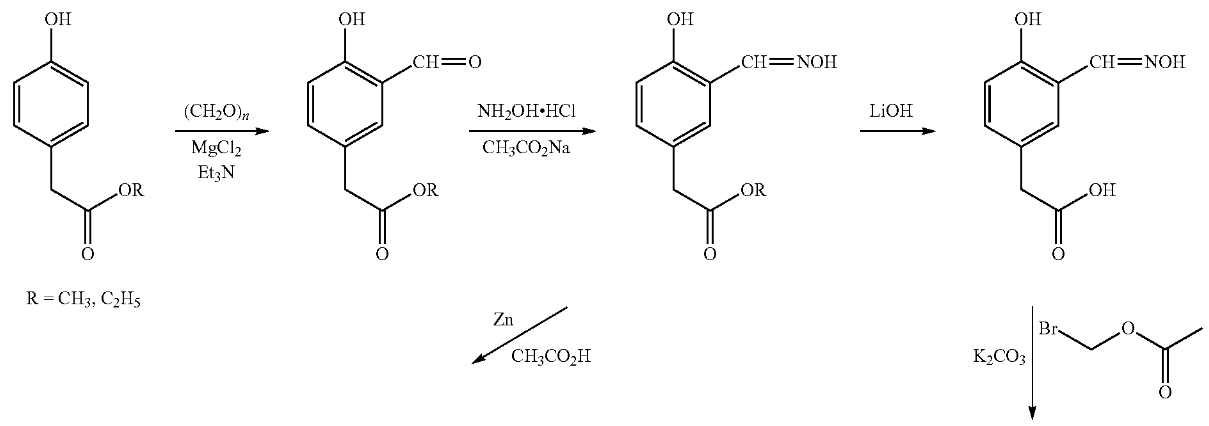

-continued

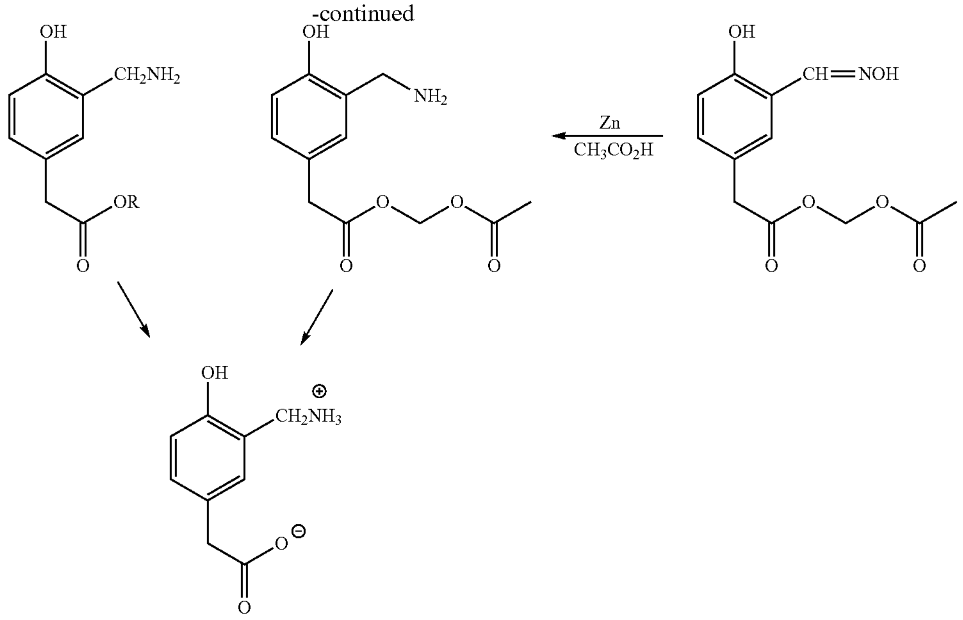

Carboxy-2HOBA

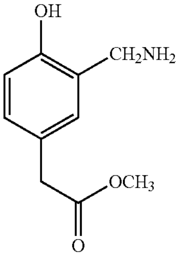

methyl
2-(3-(aminomethyl)-4-hydroxyphenyl)acetate
mcm-2HOBA

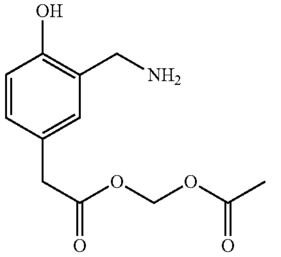

acetoxymethyl
2-(3-(aminomethyl)-4-hydroxyphenyl)acetate
AcMO-2HOBA

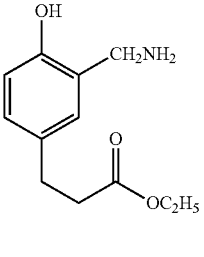

ethyl
3-(3-(aminomethyl)-4-hydroxyphenyl)propanoate
ece-2HOBA

Methyl 4-hydroxybenzoate (8.3 g) was refluxed in acetonitrile containing paraformaldehyde (8 g), magnesium chloride (10 g), and triethylamine (28 mL). After 30 m, the reaction mixture was acidified and extracted with ethyl acetate. The crude product was purified on a column of silica (5:1 hexane-ethyl acetate). The aldehyde was converted to the oxime and the latter was heated with 2 equivalents of LiOH in 1:1 methanol-water at 75-80° C. for 2 h. The oxime-acid was isolated as white solid after cooling and acidification. It (2.3 g) was dissolved in DMF (25 mL), cooled in ice and treated with $KHCO_3$ and bromomethylacetate (1.7 g). The mixture was stirred for 18 h and the crude product was purified on silica (2:1 hexane-ethyl acetate0; 2.1 g of clear liquid. The oxime was reduced with zinc powder (3.2 g) and acetic acid (30 mL) to obtain AcMO-2HOBA.

Methyl 3-formyl-4-hydroxybenzoate obtained in the first step was converted to oxime and reduced to get mcm-2HOBA. Similarly, ethyl 3-(4-hydroxyphenyl)propanoate was the starting compound for ece-2HOBA.

Synthetic Scheme for Diesters:

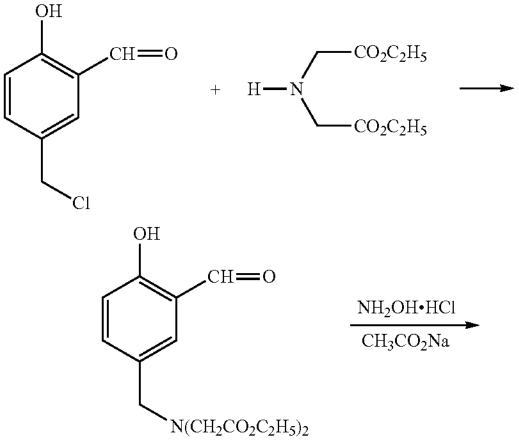

-continued

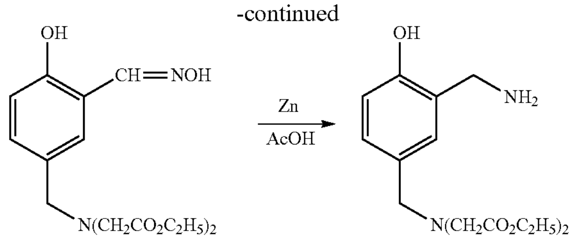

2HOBA-diester
diethyl
2,2′-((3-(aminomethyl)-
4-hydroxybenzyl)
azanediyl)diacetate 5-(Chloromethyl)-2-hydroxybenzaldehyde (8 g) was stirred with diethyl imnodiacetate (5 mL) along with triethylamine (5.6 mL) in THF (40 mL) for 2 h. The crude product was subjected to flash chromatography (silica; 3:1 hexane-ethyl acetate). The aldehyde group was converted to oxime by treating with hydroxylamine. HCl and sodium acetate in ethanol. After reduction with zinc and acetic acid, 2HOBA-diester was purified on a column of silica. The pure product was eluted with 30% methanol-ethyl acetate.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

The terms "alkoxy" and "alkoxyl" as used herein to refer to an alkyl or cycloalkyl group bonded through an ether linkage; that is, an "alkoxy" group can be defined as $—OA^1$ where $A^1$ is alkyl or cycloalkyl as defined above. "Alkoxy" also includes polymers of alkoxy groups as just described; that is, an alkoxy can be a polyether such as $—OA^1—OA^2$ or $—OA^1—(OA^2)_a—OA^3$, where "a" is an integer of from 1 to 200 and $A^1$, $A^2$, and $A^3$ are alkyl and/or cycloalkyl groups.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

It is also understood that compound described herein contain an optional counterion, if desired or necessary. Examples of these optional counterions include chloride, mesylate, bicarbonate, fluoride, nitrate, bromide, sulfate, citrate, benzoate, saccharin anion, and acetate. For example, if triphenylphosphonium compounds are described, triphenylphosphonium bromide can be assumed.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers. Additionally, unless expressly described as "unsubstituted", all substituents can be substituted or unsubstituted.

In some aspects, a structure of a compound can be represented by a formula:

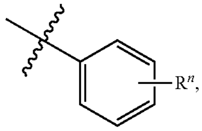

which is understood to be equivalent to a formula:

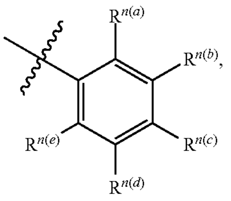

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance. Likewise, when a group R is defined as four substituents, R is understood to represent four independent substituents, $R^a$, $R^b$, $R^c$, and $R^d$. Unless indicated to the contrary, the substituents are not limited to any particular order or arrangement.

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids" includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds. The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention can comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require potentiation of metabotropic glutamate receptor activity an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

Further disclosed herein are pharmaceutical compositions comprising one or more of the disclosed compounds and a pharmaceutically acceptable carrier.

Accordingly, the pharmaceutical compositions of the present invention include those that contain one or more other active ingredients, in addition to a compound of the present invention.

The above combinations include combinations of a disclosed compound not only with one other active compound, but also with two or more other active compounds. Likewise, disclosed compounds may be used in combination with other drugs that are used in the prevention, treatment, control, amelioration, or reduction of risk of the diseases or conditions for which disclosed compounds are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient can be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element can be prior to, concurrent to, or subsequent to the administration of other agent(s).

Accordingly, the subject compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent may be co-administered, either in concomitant therapy or in a fixed combination.

In one aspect, the compound can be employed in combination with anti-hypertensive agents, anti-inflammation agents, and/or anti-oxidative stress agents. Thus, the disclosed compounds can be used in the treatment, prevention, control, amelioration or reduction of risk of the aforementioned diseases, disorders and conditions. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

In one aspect, the invention relates to methods of treatment in a mammal comprising the step of administering to the mammal at least one compound of the present invention in a dosage and amount effective to treat the indication in the mammal. In certain embodiments, the compound has a structure represented by a compound of the following formula:

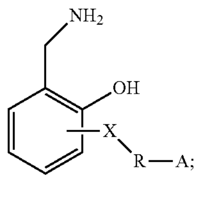

wherein:

X is a bond, alkyl, alkoxy, methoxy, —O—, or —$CH_2$—; each R is independent and chosen from $C_1$ to $C_{12}$ substituted or unsubstituted alkyl; and A is

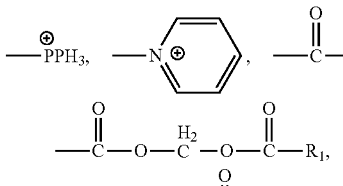

and

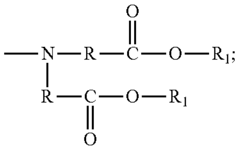

each $R_1$ is independent and chosen from $C_1$ to $C_{12}$ substituted or unsubstituted alkyl; and an optional counterion; and stereoisomers and pharmaceutical salts thereof.

In certain aspects, a subject, for example a mammal or a human, has been diagnosed with the indication prior to the administering step. In further aspects, a disclosed method can further comprise the step of identifying a subject, for example a mammal or a human, having a need for treatment of the indications, diseases, disorders and conditions described herein. In further aspects, a subject, for example a mammal or a human, has been diagnosed with a need for treatment prior to the administering step.

The disclosed compounds may be used as single agents or in combination with one or more other drugs in the treatment, prevention, control, amelioration or reduction of risk of the aforementioned indications, diseases, disorders and conditions for which compounds of the present invention or the other drugs have utility, where the combination of drugs together are safer or more effective than either drug alone. The other drug(s) may be administered by a route and in an amount commonly used therefore, contemporaneously or sequentially with a disclosed compound. When a disclosed compound is used contemporaneously with one or more other drugs, a pharmaceutical composition in unit dosage form containing such drugs and the compound is preferred. However, the combination therapy can also be administered on overlapping schedules. It is also envisioned that the combination of one or more active ingredients and a disclosed compound can be more efficacious than either as a single agent.

The compounds of the present invention can be administered with a pharmaceutically acceptable carrier. As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

Of course, one aspect of the invention relates to use of a compound of the present invention in the treatment of the indications, diseases, disorders and conditions discussed herein.

Inflammation

Inflammation is implicated in many diseases that represent major causes of morbidity and mortality in Western societies including cardiovascular diseases, acute kidney injury, and lung and heart failure. Despite use of multiple drugs, both chronic and acute inflammation still represent major health burdens. In the recent years, it has become clear that oxidative stress plays an important role in pathophysiology of many conditions associated with inflammation such as cardiovascular diseases and sepsis. Increased lipid peroxidation has been shown in hypertension, atherosclerosis and sepsis, using the clinically validated marker F2-isoprostanes. Lipid peroxidation via the isoprostane pathway produces a family of highly reactive γ-ketoaidehydes, the isolevuglandins (IsoLGs), which rapidly react with primary amines and causes cellular dysfunction. IsoLGs covalently modify and cross-link proteins by reacting with their lysine residues, and this modification can directly inhibit enzymatic functions, induce inflammation and cause cytotoxic effects. IsoLGs have been implicated in pro-inflammatory dendritic and T cell activation in hypertension. Acute treatment of isolated mitochondria with IsoLG disrupts mitochondrial respiration and promotes mitochondrial permeability transition pore (mPTP) opening, however, the role of mitochondrial IsoLGs in pathological conditions has not been investigated.

Sepsis causes devastating multi-organ failure such as acute kidney injury which is linked with increased oxidative stress and mitochondrial dysfunction. Levels of IsoLG adducts are elevated in experimental models of sepsis. Inflammation has been associated with mitochondrial dysfunction; however, its pathophysiological role and molecular mechanisms are still obscure. Mitochondria are one of the major sources of free radicals that can potentially produce IsoLG. Given the potential highly injurious nature of IsoLGs, the present inventors show that inflammation-induced IsoLGs plays an important role in mitochondrial dysfunction.

Although oxidative stress is common in multiple pathological conditions, antioxidant therapy is not currently available and common antioxidants like ascorbate and vitamin E are ineffective in the clinical studies. These agents unlikely reach important sites of free radical production such as mitochondria. Furthermore, antioxidants can potentially interfere with redox signaling increasing inflammation and tissue injury due to increased cytokine production and suppression of Nrf2 signaling.

Oxidative stress in aging and inflammation results in increased peroxidative damages to polyunsaturated fatty acids (PUFA). The cause of the isoprostane type of lipid peroxidation remained unclear. It has been proposed that autoxidation of PUFA can be initiated by perhydroxyl radical ($HO_2^•$), a protonated form of superoxide radical, which is produced in mitochondria. Hypoxia and acidification of a tissue increase production of $HO_2^•$. The present inventors show that accumulation of the oxidatively damaged mitochondrial phospholipids and IsoLG adducts is the result of PUFA oxidation by mitochondrial $HO_2^•$. The $HO_2^•$ hypothesis of the isoprostane lipid peroxidation agrees with the known fact that classical antioxidants are ineffective in prevention of this type oxidative stress and aging. Isoprostane lipid peroxidation produces racemic mixture of various forms of isoprostanes and isolevuglandins. Some of the isoprostanes can be responsible for initiation of the inflammatory responses directly while reactive IsoLG produces cytotoxic and immunogenic IsoLG-lactam adducts.

Production of IsoLG is one of the common downstream products of oxidative stress and scavenging IsoLG with 2-hydroxybenzylamine (which is not an antioxidant) reduces endothelial dysfunction, diminishes fibrosis and attenuates hypertension. Therapies specifically targeted at mitochondria represent promising strategies to reduce target-organ-damage. The present inventors show that mitochondrial targeting of the IsoLG scavenger 2-hydroxybenzylamine, by conjugating it with the lipophilic cation triphenylphosphonium, would reduce mitochondrial dysfunction and attenuate mortality associated with sepsis. The present invention explored (a) mitochondrial dysfunction in response to synthetic IsoLG and its adducts, (b) developed new mitochondria-targeted IsoLG scavenger mito2HOBA, and (c) tested if mito2HOBA protects from mitochondrial dysfunction and mortality in lipopolysaccharide (LPS) model of sepsis.

Materials and Methods

Reagents

LPS was obtained from Sigma (St Louis, MO). 2-Hydroxybenzylamine (2HOBA) and its non-scavenger analog 4-hydroxybenzylamine (4HOBA) were prepared as described previously. 15-$E_2$-IsoLG was synthesized by the method of Amarnath et al. and kept in DMSO stock solution at −80° C. All other reagents were from Sigma (St Louis, MO).

Animal Experiments

All experimental procedures were approved by Vanderbilt and Mercer Institutional Animal Care and Use Committees. The use of LPS is well-established model of bacterial sepsis in rodents (1-3). The concentrations of LPS that can be used to induce sepsis in mice depend on many factors (source of LPS, age/size, and strains of animals, desired time of response, target of interest, etc.) and may vary between different manufactures. To test the protective properties of mito2HOBA, the present inventors used LPS from *E. coli* O111:B4 (Sigma L8274). The lot of LPS tested in preliminary studies had a $LD_{50}$ of 25 μg/g at 24 hours post-injection. The same lot of LPS was used throughout entire study.

Forty C57BL/6J 3-month old mice were equally divided in four groups: Sham (Control), LPS-injected mice (LPS), mice supplemented with mito2HOBA (0.1 g/Liter) in the drinking water (mito2HOBA), and LPS-injected mice pretreated with mito2HOBA in the drinking water (LPS+mito2HOBA). Sepsis-induced mortality among animals was used to evaluate the protective role of mito2HOBA. Mortality was assessed regularly several times per day for three consecutive days. In additional experiments mice were sacrificed after 24 hours of LPS injection to analyze mitochondrial complex I and complex II activities.

Mitochondrial Studies

All procedures for mitochondrial isolation, respiration analysis and respiratory chain enzymology have been previously described. Mitochondrial complex I and complex II activities were evaluated after 24 hours of LPS injection as described above. Mitochondria were isolated from 12-14-week-old male C57BL6/6J mouse kidneys. For respiration studies, electrons were entered at either complex I (glutamate+malate as substrate) or complex II (succinate as substrate). Mitochondria in some organs, e.g. brain, oxidize up to 50% of pyruvate and glutamate via transamination to α-ketoglutarate and further conversion to succinate. Since kidney mitochondria are much less studied than mitochondria from other organs, the present inventors used the specific inhibitor of Complex II malonate (5 mM) to evaluate the alternative pathways for glutamate oxidation. The Complex II mediated respiration was defined as malonate-inhibited oxygen consumption while Complex I specific respiration was defined as malonate resistant oxygen consumption.

Respiration rates were measured using Fluorescence Lifetime Micro Oxygen Monitoring System (Instech Laboratories, Inc.). Two oxygen consumption rate measurements were performed for each substrate and each run included additions of 0.24 mg/ml protein, ADP (125 μM) to stimulate state III and subsequent state IV respiration. OXPHOS specific enzyme activities in submitochondrial particles (SMP) were measured using a Varian Cary 300 Bio UV/Vis spectrophotometer with temperature controlling cell holder. Briefly, SMP were prepared by sonication of isolated organelles. Complex I activity was monitored in triplicate samples as the reduction of 10 μM decylubiquinone at 272 nm by 15 μg of mitochondrial protein with 40 μM NADH. Using this method, 90-100% of the total complex I activity is sensitive to rotenone inhibition. Complex II activity was measured by monitoring the absorbance at 600 nm during the oxidation of 50 μM DCPIP as artificial electron acceptor by 65 μM ubiquinone in presence of 2 mM KCN and 2 μg/ml rotenone and antimycin A.

Analysis of Complex I and Complex II Mediated Respiration in Kidney Mitochondria In order to define specific alterations in the mitochondrial respiration in LPS model of sepsis and test the potential protection by mito2HOBA the present inventors adopted the Seahorse protocol for mitochondrial studies in the presence of mitochondrial substrates Glutamate+Malate (GM) or succinate. To define the specific role of complex I mediated respiration the present inventors performed measurements in the presence of complex II inhibitor malonate (5 mM). The present inventors measured basal respiration in the presence of mitochondria plus substrates, coupled respiration after addition of ADP (2 mM), proton leak following addition of oligomycin A (2.5 μM) uncoupled respiration after supplementation of CCCP (1 μM) and non-mitochondrial respiration with mixture of antimycin A and rotenone (1 μM) Mitochondrial studies where independently verified in two labs using Oroboros O2k high-resolution respirometry and Fluorescence Lifetime Micro Oxygen Monitoring System (Instech Laboratories, Inc). Kidney mitochondria were isolated from control sham mice, LPS-injected mice (25 μg/g, 16 hours post-injection), mito2HOBA supplemented mice (0.1 g/Liter drinking water, 4 days), or mito2HOBA plus LPS (0.1 g/Liter mito2HOBA for 3 days plus LPS injection). One kidney was used for mitochondrial studies and second kidney was used for histopathological studies.

Kidney Histological Analyses

Kidneys were harvested from mice and placed immediately in 10% formalin. Following fixation, kidneys were washed with saline, placed in 70% ethanol, and processed in the following sequence: 70% ethanol; 80% ethanol; 95% ethanol; 100% ethanol; 100% xylene. Then kidneys were embedded in POLY/Fin paraffin (ThermoFisher). Five-μm sections were cut using a Leitz 1512 microtome and were mounted on glass slides. Sections were stained with hematoxylin and eosin and were viewed using an Olympus IX70 microscope. Images were captured with a Jenoptix Progress C12 digital camera. Histopathological scores of kidneys were measured as follows: (0) No tubular injury; (1) <10% tubules injured; (2) 10-25% tubules injured; (3) 25-50% tubules injured; (4) 50-75% tubules injured; (5) >75% tubules injured.

Figure 7:
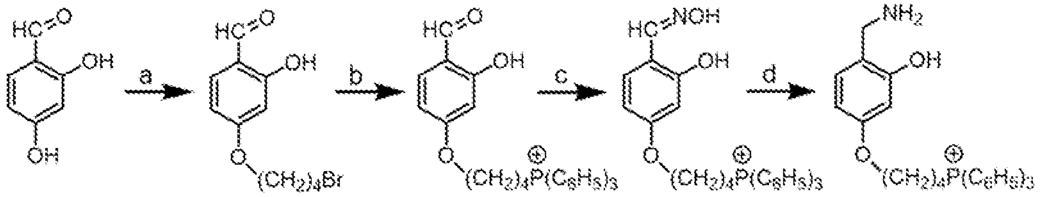
FIGS. 7A and 7B show (A) the synthesis of an example of a mitochondria targeted compound of the present invention and (B) that this compound is an effective scavenger of IsoLG.
Figure 7:
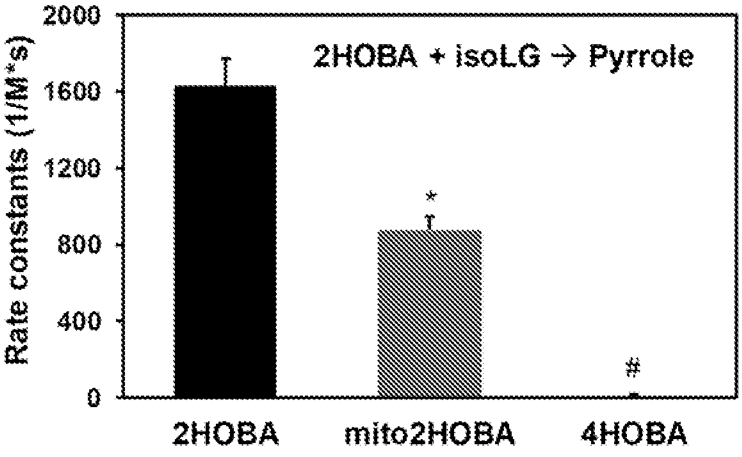

Synthesis of Mitochondria-Targeted IsoLG Scavenger Mito2HOBA (See FIG. 7)

Cesium carbonate (4.9 g, 15 mmol) was added to 2,4-dihydroxybenzaldehyde (4.2 g, 30 mmol) and 1,4-dibromobutane (6.6 g, 30 mmol) in acetonitrile (50 ml). The mixture was heated at 80° C. under argon for 5 h, cooled and added to 1 M phosphate buffer, pH 7 (30 ml), ice and $KH_2PO_4$ (2 g) with mixing. The solid was removed by filtration and the filtrate was extracted with ethyl acetate. Purification by column (silica, 9:1 hexane-ethyl acetate) yielded 4-(4-bromobutoxy)-2-hydroxybenzaldehyde (4.1 g, 50%). It was mixed with triphenylphosphene (4.2 g) in toluene (75 ml) and refluxed under argon for 15 h. The pink solid was purified by flash chromatography (0-10% methanol in dichloromethane to get 4-(4-formyl-3-hydroxyphenoxy)butyl)triphenylphosphonium bromide (4.8 g, 60%). The aldehyde was converted to oxime by stirring with $NH_2OH \cdot HCl$ (0.63 g) and $CH_3CO_2Na$ (0.74 g) in ethanol (40 ml) for 1 h. The crude product (5.6 g) was dissolved in acetic acid (60 ml). Zinc powder (6 g) was added and the suspension was heated in a water bath (60° C.) for 1 h. The mixture was cooled, filtered through Celite. The filtrate was evaporated and co-evaporated with toluene (3×10 mL) and ethanol (15 mL). The residue was heated in hot 2-propanol (200 ml), filtered and cooled to obtain pure mito2HOBA; 3.0 g; MS m/z 456 ($M^+$).

Statistics.

Data were analyzed using the Student-Neuman-Keuls post-hoc test and analysis of variance (ANOVA). P levels <0.05 were considered significant.

Results

Isolevuglandins Impaired Mitochondrial Respiration

Complex I is a key component of mitochondrial oxidative phosphorylation. Inactivation of complex I can lead to reduced ATP production and tissue damage. Addition of IsoLG to cells produces both protein—adducts and IsoLG-phosphatidylethanolamine adducts (IsoLG-PE) which can independently contribute to mitochondrial dysfunction. The present inventors tested whether IsoLG or IsoLG-PE could contribute to mitochondrial dysfunction. Five-minute treatment of isolated mitochondria with 15-$E_2$-IsoLG-PE (20 μM) inhibited state 3 respiration by 41% while similar doses of 15-$E_2$-IsoLG reduced state 3 respiration by 74% in the presence of complex I substrates glutamate+malate (FIG. 1A). These data support the potential role of IsoLG-PE and IsoLG-protein adducts in mitochondrial dysfunction. To further define the potential targets of IsoLG in mitochondria, the present inventors studied the effect of IsoLG and IsoLG-PE on complex I- and complex II-mediated respiration.

Acute addition of a low dose of 15-$E_2$-IsoLG (0.5 μM) significantly attenuated complex I-mediated respiration, but complex II respiration was much less affected (FIG. 1B,C). Treatment of intact mitochondria with a low dose of 15-$E_2$-IsoLG-PE partially diminished complex I respiration but did not affect complex II respiration. These data directly demonstrate the impairment of mitochondrial respiration by IsoLG and IsoLG-PE.

IsoLG and IsoLG Adducts Inhibit Complex I Activity

The present inventors hypothesized that IsoLG can directly affect the complex I and complex II activity. To test this hypothesis, the present inventors studied the activity of complex I and complex II in mitochondrial lysates treated with a bolus of IsoLG. It was found that IsoLG causes robust complex I inactivation by 74% while complex II activity was inhibited by only 21% (FIG. 2A). These data showed that complex I respiration is particularly sensitive to IsoLG.

As shown above, both IsoLG and IsoLG-PE diminish complex I-mediated respiration, therefore, complex I could be affected by IsoLG directly or inhibited by low-molecular IsoLG adducts. The present inventors tested the inhibition of complex I by IsoLG adducts compared with bolus IsoLG. Supplementation with IsoLG modified-ethanolamine (IsoLG-ETN), modified L-Lysine (IsoLG-Lys), or modified-PE (IsoLG-PE) inhibited complex I activity by more than 80%, similar to the effect of bolus IsoLG (FIG. 2B). Interestingly, IsoLG modified spermine (IsoLG-spermine) did not affect complex I, suggesting that natural poly-amines could potentially protect complex I from IsoLG mediated inhibition. These data demonstrate that complex I is directly inhibited by low-molecular IsoLG adducts such as IsoLG-Lys and IsoLG-PE; thus, these adducts may mediate the impairment of complex I induced by direct addition of IsoLG. These data directly confirm that IsoLG-mediated inhibition of complex I contribute to mitochondrial dysfunction.

Mitochondria-Targeted IsoLG Scavenger Mito2HOBA

Figure 3:
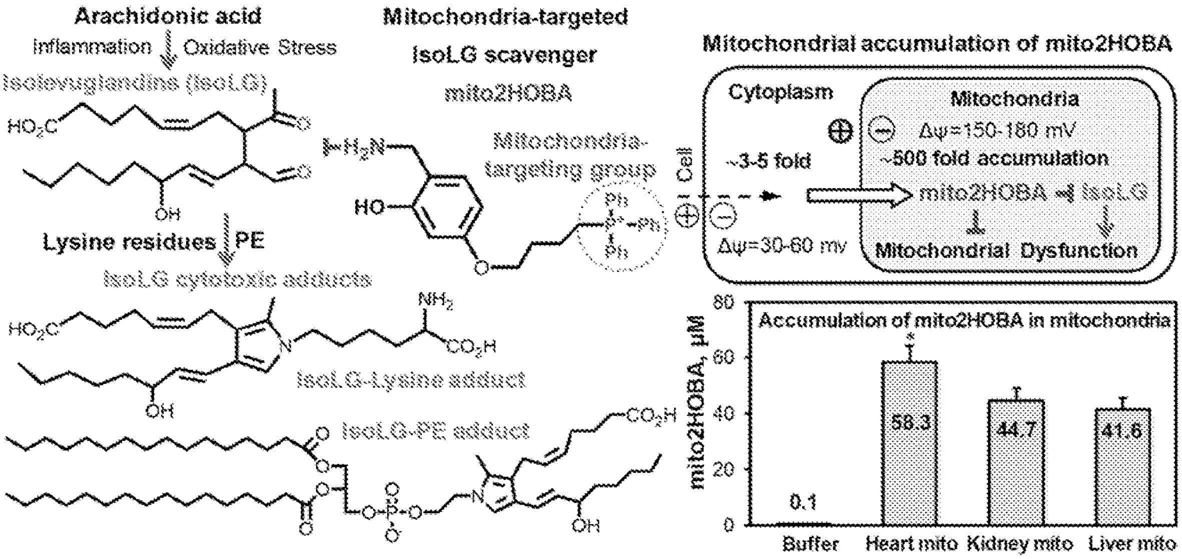
FIG. 3 shows mitochondria-targeting of IsoLG scavenger mito2HOBA. Linking the 2-hydroxybenzylamine to lipophilic cation triphenylphosphonium directs mito2HOBA to mitochondria since its membrane potential is much higher than in other organelles within cells leading to selective accumulation within mitochondria. Inflammation and oxidative stress oxidize arachidonic acid to reactive IsoLG which react rapidly with protein lysine residues and phosphatidylethanolamine yielding cytotoxic IsoLG adducts. Incubation of mito2HOBA (0.1 μM) with isolated mitochondria (1 mg/ml) causes robust accumulation of mito2HOBA in the mitochondrial fractions. Data are expressed as mean±STD (N=4). Mitochondria-targeted mito2HOBA can potentially reduce mitochondrial dysfunction by scavenging of IsoLG in the mitochondrial matrix.

To test the hypothesis that specific scavenging of IsoLG in mitochondria improves mitochondrial function, the present inventors developed a mitochondrial-targeted IsoLG scavenger, mito2HOBA, by conjugating the lipophilic cation triphenylphosphonium to 2-hydroxybenzylamine (FIG. 3). The membrane potential of mitochondria within living cells is negative inside (−150 mV). As this membrane potential is much higher than in other organelles within cells, lipophilic cations such as triphenylphosphonium selectively accumulate within mitochondria. Molecules conjugated to triphenylphosphonium are therefore targeted to the mitochondria. For example, mitoTEMPO is concentrated within the mitochondrial matrix by more than a five hundred-fold.

Mito2HOBA is a water-soluble compound which can be supplied in the media and provided to animals in the drinking water. In animal experiments, mito2HOBA was well tolerated in doses from 0.1-0.3 g/L. Mass spectrometric analysis of kidney and heart mitochondria isolated from mice that received mito2HOBA in their drinking water (0.1 g/L) for 5-days confirmed that mito2HOBA predominantly accumulated in the mitochondrial fraction (by 80%) at μM levels. Likewise, incubation of isolated mitochondria with mito2HOBA (0.1 μM) causes robust accumulation of mito2HOBA in the mitochondrial pellet by 400 to 600-fold (FIG. 3).

In order to confirm the IsoLG scavenging properties of mito2HOBA, the present inventors studied its reaction with the IsoLG analog 4-oxopentanal as the present inventors described previously. Mito2HOBA was highly reactive with 4-oxopentanal with a reaction rate constant that was about 50% of 2HOBA itself (Supplemental FIG. 1S). The slightly reduced reaction rate may be due to steric hindrance by the bulky triphenylphosphonium group. The overall rate of IsoLG scavenging in physiological conditions depends both on the rate constant and the local concentration of the scavenger (V=k*[mito2HOBA]*[IsoLG]). Of note, 2HOBA analogs do not scavenge oxidants such as $O_2^{\bullet-}$ and peroxynitrite. The present inventors show that supplementation with mito2HOBA at low submicromolar level would result in low cytoplasmic level but significant mitochondrial accumulation (FIG. 3) as the present inventors had previously described for mitochondria-targeted mitoTEMPO. This will result in low level of mito2HOBA in cytoplasm but high mitochondrial accumulation leading to specific scavenging of IsoLG in mitochondria (FIG. 3).

Complex I- and Complex II-Mediated Kidney Respiration in LPS and Mito2HOBA Treated Mice The kidney has a high demand for energy and renal mitochondria can potentially oxidize glutamate via transamination to α-ketoglutarate and further conversion to succinate. The present inventors analyzed mitochondrial respiration in the presence of Glutamate+Malate (GM), succinate and used Complex II inhibitor malonate to measure the specific Complex I mediated respiration. Malonate inhibited 58% of glutamate-driven respiration (FIG. 4A) supporting the metabolic plasticity of renal mitochondria. Interestingly, LPS injection reduced both GM- and succinate-mediated respiration, and substantially diminished complex I-specific oxygen consumption in the presence of GM+malonate (FIG. 4B). LPS significantly increased mitochondrial protein leak with both substrates indicating uncoupling of mitochondrial respiration. Mito2HOBA alone slightly reduced succinate-driven respiration and improved complex I-specific oxygen consumption in the presence of GM+malonate (FIG. 4C). Furthermore, mito2HOBA supplementation significantly protected from LPS-induced impairment of GM-mediated respiration and complex I-specific oxygen consumption in the presence of GM+malonate but did not affect the succinate mediated respiration or mitochondrial protein leak (FIG. 4D).

Mito2HOBA Reduces Mitochondrial Dysfunction and Attenuates Mortality in LPS Model of Sepsis To test the role of IsoLG-mediated mitochondrial dysfunction the present inventors supplemented mice with novel mitochondria-targeted IsoLG scavenger mito2HOBA (0.1 g/L). Treatment with LPS (25 μg/g by body weight) caused severe mortality but treatment with mitochondria-targeted IsoLG scavenger mito2HOBA increased animal survival at 96 hours post-injection by 3-fold (FIG. 5A). Additional studies showed that complex I/complex II activity ratio was markedly decreased in mitochondria isolated from the kidneys of LPS-treated mice compared to vehicle treated mice (FIG. 5B). Supplementation of mice with mito2HOBA completely preserved the complex I/complex II activity ratio even after LPS treatment. These data support the role of mitochondrial IsoLG in the mitochondrial dysfunction and mortality associated with sepsis.

Mito2HOBA Protects Against LPS-Induced Renal Injury

Figure 5:
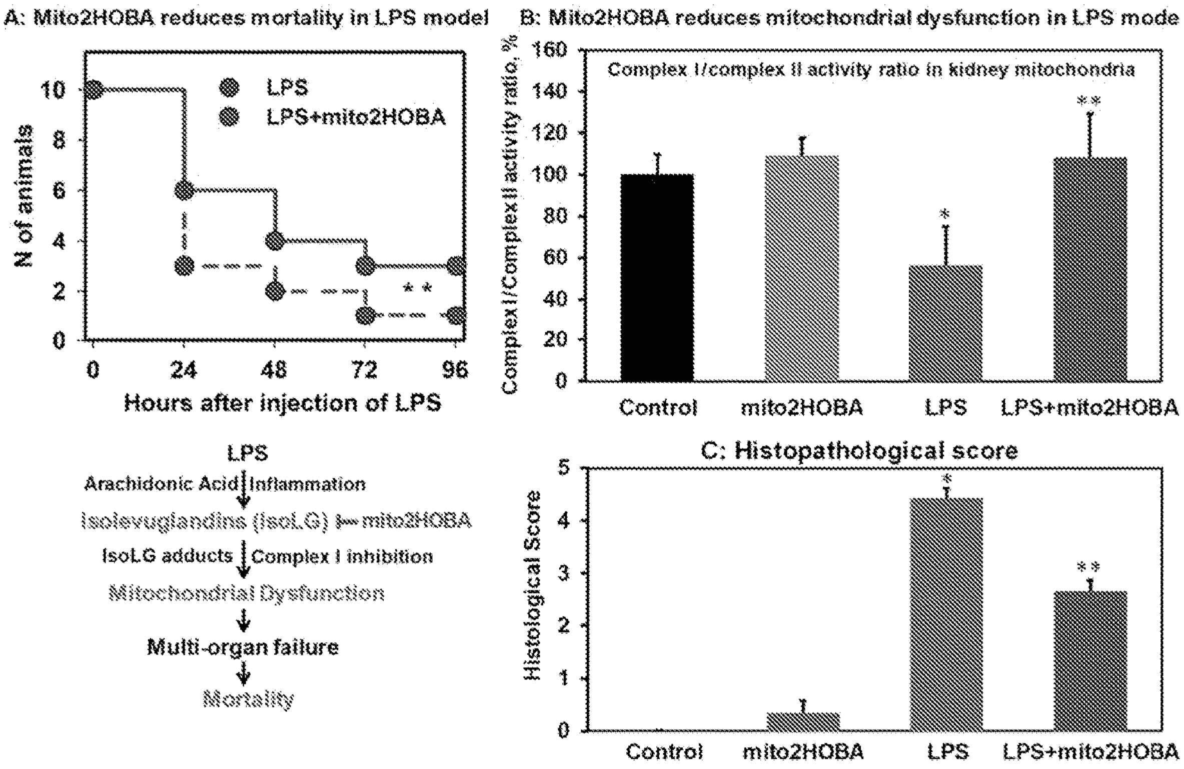
FIG. 5 shows animal survival (A), Complex I/Complex II activity ratio (B) and (C) histopathological scores in Control, mito2HOBA-supplemented and LPS treated mice. Three months old C57BL/6J mice (25-28 g) were supplemented with mito2HOBA (drinking water, 0.1 g/L) for 72 hours prior to LPS injection (25 μg/g). Complex I/Complex II activity ratio is expressed as a % compared to Control (100%). (C) Histopathological scores of renal injuries as described in methods section. Quantitative analysis of cellular injury shows that treatment with mito2HOBA leads to a significant reduction in cellular injury compared with treatment with LPS alone. Data are mean±STD *P<0.01 vs LPS (n=6), *P<0.01 vs LPS (n=10).
Figure 6:
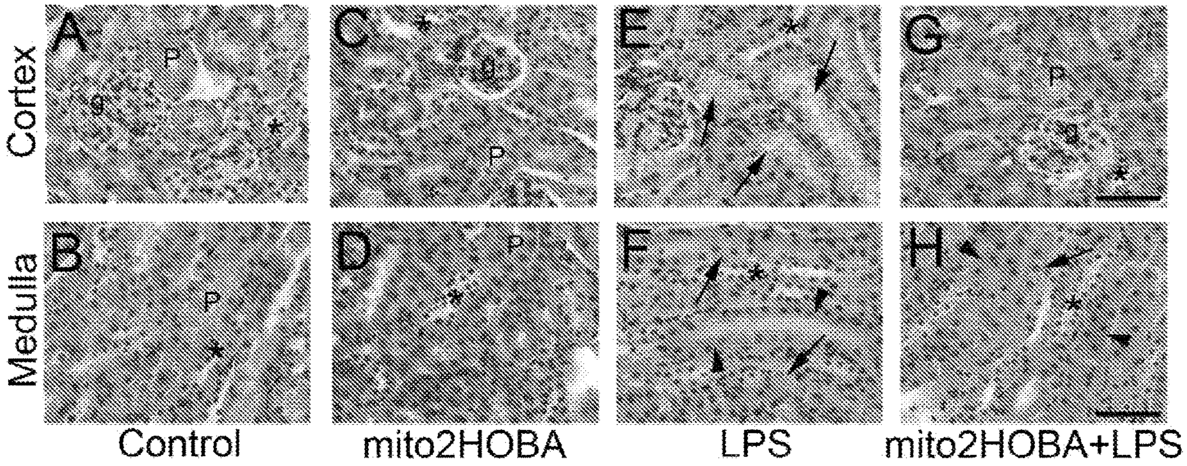
FIGS. 6A-H show histological analysis of cellular injury in kidneys of control, mito2HOBA supplemented, LPS-injected and LPS+mito2HOBA-treated mice. Representative sections from control mice show normal glomeruli (g), proximal tubules (P), and distal tubules (*) in the cortex (A) and medulla (B). Sections of kidney from mice treated with mito2HOBA alone (C & D) were very similar to those from control mice. While most tubules appeared normal, a small number of proximal tubular cells in the medulla (D) showed slight evidence of cytoplasmic vacuolization. There was no evidence of injury in the cortex (C). In contrast, sections of kidney from mice treated with LPS show vacuolization and cellular degeneration (arrows) in the cortex (E) and medulla (F). In the medulla, numerous proximal tubular cells stained basophilic (arrowheads) suggesting alterations in intracellular metabolism. Distal tubules (*) appeared normal. When mice were treated with LPS and mito2HOBA, cellular injury was detected in medulla (H) while the cortex (G) appeared normal. The overall injury was greatly reduced compared with that of mice treated with LPS. In the medulla, small areas of cytoplasmic degeneration (arrows) and basophilic staining (arrowheads) were evident. Scale bar=50 μm.

Histological analyses of kidneys were performed to provide visual evidence of mito2HOBA protection (FIG. 6). The cortex and medulla of control kidneys appeared normal with no evidence of injury. In contrast, kidneys of mice treated with LPS demonstrated significant cellular injury. Numerous areas of vacuolization and cellular degeneration (arrows) were identified in the cortex and medulla of kidneys from LPS-injected mice. In the medulla, numerous proximal tubules stained basophilic (arrowheads) suggesting alterations in intracellular metabolic processes. Similar to control mice, kidneys of mice supplemented with mito2HOBA appeared normal. A few small areas of cellular degeneration were scattered sparsely throughout the medulla (not pictured). When mice were treated with LPS plus mito2HOBA, the cortex appeared normal while cellular injury was evident in the renal medulla. Small areas of cellular degeneration and basophilic staining were observed throughout the medulla, but the extent and degree of injury was less than that in kidneys of mice treated with LPS alone. As shown quantitatively in FIG. 5C, mito2HOBA appeared to be protective against LPS-induced cellular injury.

Discussion

Figure 2:
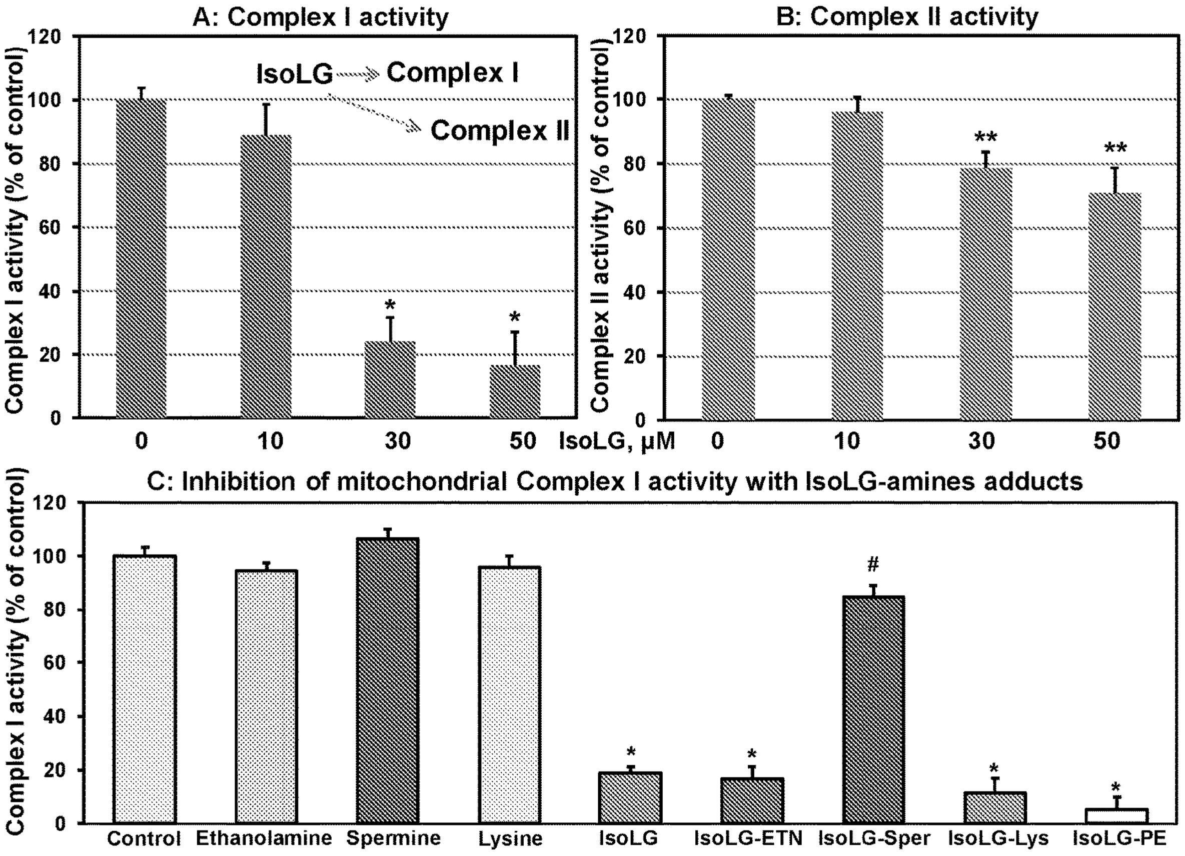
FIG. 2 shows inhibition of complex I and complex II activity by IsoLG and IsoLG-adducts. (A, B) Mouse kidney mitochondrial lysate was incubated with DMSO (vehicle) or IsoLG for 5-minites prior to analysis of complex I or complex II activity as described previously [29, 30]. *P<0.01 vs Sham. **P<0.05 vs Sham. (C) Mouse kidney mitochondrial lysate was acutely treated with DMSO (Control), ethanolamine, spermine, L-lysine, IsoLG (1.5 μM) or IsoLG modified-ethanolamine (IsoLG-ETN, 1.5 μM), -spermine (IsoLG-Sper, 1.5 μM), L-lysine (IsoLG-Lys, 1.5 μM), -phosphatidylethanolamine (IsoLG-PE, 1.5 μM) prior to measurements of complex I activity expressed as a % of Control (100%). Data are expressed as mean±STD (N=3-6). *P<0.001 vs Sham, #P<0.01 vs IsoLG.

The present inventors show that IsoLG or its stable adduct IsoLG-PE impair mitochondrial respiration, particularly complex I-mediated respiration in the presence of malate and glutamate (FIG. 1). Experiments in mitochondrial lysates show that IsoLG and IsoLG adducts specifically inhibited complex I activity (FIG. 2). Furthermore, the present inventors showed that a mitochondria-targeted form of a known IsoLG scavenger 2HOBA (FIG. 3) markedly protected against renal injury and animal mortality in LPS-induced sepsis model (FIG. 5,6).

Impaired oxidative phosphorylation significantly contribute to organ damage in sepsis. Mitochondrial dysfunction in sepsis was recently linked to complex I damage, and targeted protection of complex I was proposed as a treatment for sepsis. Sepsis was previously shown to increase IsoLG production and IsoLG can induce the mitochondrial permeability transition. The present inventors show that IsoLG might also mediate the mitochondrial dysfunction found in sepsis. Indeed, the data indicates that complex I activity is particularly sensitive to IsoLG and IsoLG adducts suggesting that sepsis-induced IsoLG likely inhibits complex I activity to promote mitochondrial dysfunction. Consequently, this pathway may be important for the multi-organ failure induced by sepsis.

Figure 4:
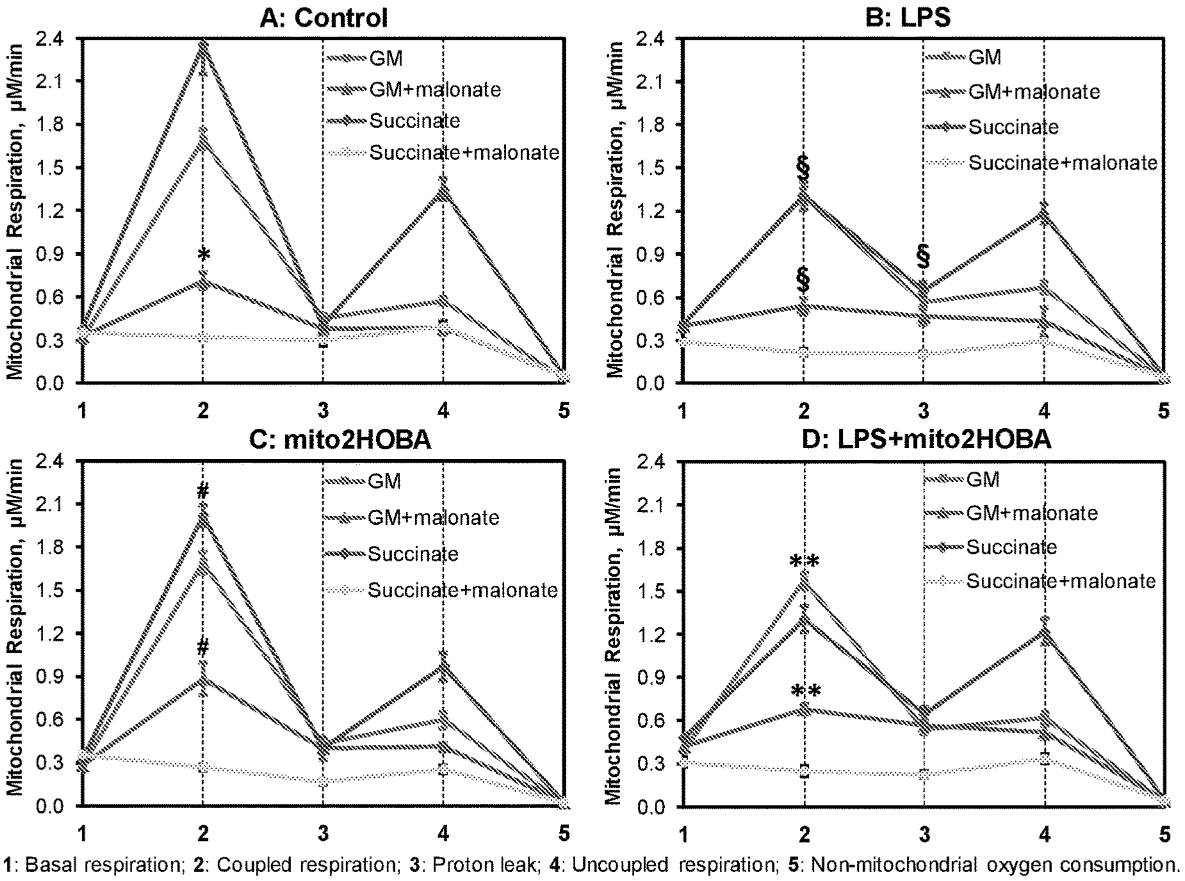
FIG. 4 shows respiration of kidney mitochondria isolated from control sham, mito2HOBA-supplemented, LPS treated and LPS plus mito2HOBA mice. To study the mitochondrial function, the combination of glutamate and malate (GM) or succinate was used as substrates. Since glutamate can be converted via transamination to α-ketoglutarate and further to succinate, the present inventors used complex II inhibitor malonate to define specific complex I respiration. The basal respiration (1) was measured in mitochondria supplemented with respiratory substrates. Then ADP was added to measure the coupled respiration (2). The proton leak (3) was determined after addition of complex V inhibitor oligomycin A. The uncoupled respiration (4) was measured after supplementation with CCCP. Finally, antimycin A plus rotenone were added to assess non-mitochondrial respiration (5) as described previously [32]. Data are mean±STD (n=4-6). *P<0.001 vs GM, #P<0.01 vs Control, § P<0.001 vs Control, **P<0.01 vs LPS.

It is well known that with NADH and the NAD-dependent substrates the rate of respiration is limited by the FAD-dependent NADH dehydrogenase of Complex I. Therefore, all downstream sites of the respiratory chain remain oxidized and produce very little reactive oxygen species. Organs requiring fast ATP production use oxidation of succinate produced via transamination of pyruvate or glutamate in order to accelerate the rates of mitochondrial respiration and ATP production. The present inventors have previously shown that brain mitochondria utilize this pathway, and now the present inventors show for the first time that kidney mitochondria also adopt to high energy demands by diverting the mitochondrial metabolite flux to succinate to feed the Complex II mediated respiration. Complex II is a much simpler protein and it has higher abundance compared to Complex I. Interestingly, it is seemingly much less sensitive to the damaging effects of inflammation in the LPS model (FIG. 4,5). Meanwhile, it should be noted that higher respiration rate by Complex II has substantial pitfalls since it drives overproduction of mitochondrial reactive oxygen species via reverse electron transport. The succinate mediated oxidant production contributes to brain and heart injury, and succinate-driven reverse electron transport has been proposed as a new therapeutic target. The data show that LPS induces switch from complex I to complex II respiration, however, this maladaptation can promote kidney damage and inflammation similarly to the previously reported succinate driven cardiac injury. Analysis of specific substrate utilization showed significant decrease in complex I, II and IV and fatty acid-mediated respiration in kidney mitochondria in LPS-induced sepsis. The data show that mito2HOBA protects mitochondria and reduces cellular injury; however, the specific targets of mitochondrial IsoLG remain elusive. IsoLG can potentially attenuate functions of multiple mitochondrial complexes and diminish mitochondrial metabolism of fatty acids. Further studies are warranted to elucidate the specific pathophysiological role of mitochondrial IsoLG. Sepsis induces kidney inflammation, renal tubular cell injury, apoptosis and mitochondrial swelling and treatment with mitochondria-targeted inhibitor of lipid oxidation, SS-31, reduces sepsis-induced organ dysfunctions. The data support the protective effect of mito2HOBA from pathological alterations in sepsis.

Mitochondrial dysfunction in sepsis was recently linked to complex I damage and targeting complex I was proposed in sepsis. In this work the present inventors have demonstrated the potential role of IsoLGs and IsoLG adducts in inhibition of complex I and therapeutic effect of mito2HOBA on complex I function. The present inventors show that targeting the mitochondrial IsoLGs improves the mitochondrial respiration and rescue from mitochondrial dysfunction in conditions associated with inflammatory injury.

To show the role of IsoLG in inflammation-induced mitochondrial dysfunction, the present inventors developed the mitochondria-targeted IsoLG scavenger mito2HOBA. Driven by its lipophilic triphenylphosphonium moiety, mito2HOBA robustly accumulated in the mitochondria of multiple organs such as kidney, heart and liver. At 0.1 g/L in drinking water, mito2HOBA was well tolerated by mice. Mito2HOBA showed significant protective effects in the LPS model of sepsis. Indeed, mito2HOBA supplementation reduces animal immediate and extended mortality by 3-fold and mito2HOBA completely preserves complex I/complex II activity ratio in LPS-treated mice. Treatment with mito2HOBA also eliminated injury to tubules in the renal cortex and significantly reduced cellular degeneration and injury in medullary tubules. The rapid effect of mito2HOBA could potentially improve outcomes in the clinical settings, as it can give additional time for medical personnel to perform additional live-saving procedures for septic patients. Overall, these data support the role of mitochondrial IsoLG in mitochondrial dysfunction and therapeutic potential of mitochondria-targeted IsoLG scavenger mito2HOBA.

The present inventors also show that targeting mitochondrial IsoLG may be more effective than simply targeting mitochondrial ROS production. Kozlov and colleagues proposed that mitochondrial ROS accelerates inflammatory response and promotes the end-organ-damage, so targeting of mitochondrial ROS would be an effective treatment for inflammation. Indeed, treatment of LPS-treated rats with the mitochondria-targeted antioxidants mitoTEMPO and SkQ1 reduced the expression of inducible nitric oxide synthase and diminished markers of organ damage. However, these mitochondria-targeted antioxidants also increased the markers of organ damage at earlier time points suggesting the potential interference of the antioxidants with cell signaling needed to activate protective responses. Furthermore, recent studies of cecal ligation and puncture sepsis model also showed a lack of survival benefit of mitochondrial antioxidants. Whether the apparent contradictory effects observed in these previous studies can be attributed to the specific model of sepsis, the animal species used, or the magnitude of the sepsis insult is unclear. Genetic ablation of NADPH oxidase in p47phox-deficient mice, a major non-mitochondrial source of ROS, exaggerated LPS-induced NF-κB activation, increased expression of proinflammatory cytokines in lungs, increased neutrophilic alveolitis and sustained greater lung injury compared with wild-type mice. Of note, 2HOBA derivatives do not scavenge ROS such as $O_2^{\bullet}$— and peroxynitrite, and, therefore, mito2HOBA will not interfere with cell redox signaling as many antioxidants described previously. These data suggest potentially diverse roles of ROS in sepsis and the importance of targeting of specific cells and subcellular compartments such as mitochondria.

The present inventors tested the potential role of IsoLGs in mitochondrial dysfunction and mortality associated with sepsis using new mitochondria-targeted IsoLG scavenger mito2HOBA (see graphical Abstract and FIG. 5 scheme). The present inventors also show that IsoLG can be produced by multiple enzymatic and non-enzymatic pathways, and that scavenging of mitochondrial IsoLG can specifically attenuate mitochondrial dysfunction and cell injury associated with inflammation. Interestingly, mitochondria-targeted antioxidants MitoQ and MitoE attenuate mitochondrial lipid peroxidation, reduce interleukin-6, improve mitochondrial function and diminish the markers of organ dysfunction in rat model of LPS-induced sepsis which is in line with pathophysiological role of IsoLG produced by lipid peroxidation in isoprostane pathway. Thus, the present invention shows the potential therapeutic benefit of specifically targeting mitochondrial IsoLGs.

Hypertension

To test the role of mitochondrial isoLGs in hypertension, the present inventors studied the accumulation of mitochondrial isoLG-protein adducts in normotensive and hypertensive human subjects and in angiotensin II mouse model of hypertension using mass spectrometry and Western blot analysis. The therapeutic potential of targeting mitochondrial isoLGs was tested by novel mitochondria-targeted isoLG scavenger mito2HOBA. The results showed substantial accumulation of mitochondrial isoLG protein adducts in vascular and kidney tissues in hypertension. Furthermore, mito2HOBA treatment of arterioles from hypertensive subjects increases SOD2 deacetylation and reduces mitochondrial superoxide in human aortic endothelial cells. In mice, mito2HOBA prevents accumulation of mitochondrial isoLG-protein adducts, reduces acetylation of SOD2 and CypD, protects mitochondrial respiration, preserves ATP production, blocks mitochondrial permeability pore opening, reduces vascular superoxide, protects endothelial NO, improves endothelium-dependent relaxation, and attenuates hypertension. These data show that mitochondrial isoLGs promote mitochondrial and endothelial dysfunction and scavenging of mitochondrial isoLGs may have therapeutic potential in treatment of vascular dysfunction and hypertension.

Materials and Methods

Reagents

Dihydroethidium (DHE) and MitoSOX superoxide probes were supplied by Invitrogen (Grand Island, NY). Sirt3 (54905) antibodies were from Cell Signaling. Acetyl-K68-SOD2 (ab137037), complex I NDUFS1 75 kDa subunit (ab22094) and CypD (ab110324) and GAPDH (ab8245) antibodies were from Abcam. SOD2 (sc30080) antibodies were obtained from Santa Cruz Biotechnology. Acetyl-lysine antibodies (ab3839) were provided by Millipore-Sigma. D11, an isoLG-lysyl adducts-specific scFv antibody, has been previously characterized. All antibodies were used at 1000-fold dilution. 2-Hydroxybenzylamine (2HOBA), mitochondria-targeted isoLG scavenger mito2HOBA and isoLG inactive analog 4-hydroxybenzylamine (4HOBA) were synthesized as described previously. All other reagents were obtained from Sigma (St Louis, MO).

Animal Experiments

Hypertension was induced by angiotensin II (0.7 mg/kg/min) as described previously. To test the therapeutic potential of scavenging of mitochondrial isoLGs, wild-type C57B1/6J male and female mice (Jackson Labs) received saline or angiotensin II minipump placement, and provided with the plain water (vehicle) or mito2HOBA in the drinking water (0.1 g/liter). Blood pressure was monitored by the telemetry and tail-cuff measurements as previously described. The Vanderbilt Institutional Animal Care and Use Committee approved the procedures (Protocol M1700207). Simple randomization was used to select animals for sham, angiotensin II or mito2HOBA groups for equal chance of being allocated to treatment groups.

Kidney Mitochondria Isolation

C57B1/6J mice were sacrificed by carbon dioxide and kidneys removed, cleaned from fat tissue and placed in the ice-slurry cold isolation medium. In a cold room, kidneys were minced, washed with the isolation medium and homogenized using a Polytron disintegrator with two pulses of 2 seconds each. Homogenate was diluted 7-fold (w/v) and mitochondria were isolated by differential centrifugation and purified with Percoll gradient. Isolation medium contained 75 mM mannitol, 175 mM sucrose, 20 mM MOPS, pH 7.2, 1 mM EGTA. Mitochondrial protein concentration was measured by Bradford method.

Measurements of Mitochondrial IsoLGs by Mass Spectrometry

IsoLG-Lysyl-Lactam adducts were measured in mitochondria isolated from the kidneys of sham or angiotensin II-infused mice using Mass Spectrometry. Mitochondrial proteins were subjected to complete enzymatic digestion to individual amino acids. A [$^{13}C_6$] internal standard was added and the isoLG-lysyl adducts were purified by solid phase extraction and HPLC before being quantified by Liquid Chromatography-tandem Mass Spectrometry assay (LC/ESI/MS/MS) using isotopic dilution as described previously.

Measurements of Cardiolipin Oxidation

Cardiolipin oxidation in human aortic endothelial cells was measured by Liquid Chromatography-Mass Spectrometry (LC/MS) as described previously.[44] The extracted lipid fraction was separated online by UPLC using a Waters Acquity UPLC system (Waters Corp., Milford, MA). Mass Spectrometry analysis was performed on a Thermo Quantum Ultra triple quadrupole mass spectrometer (Thermo Scientific Inc., San Jose, CA, USA).

Measurement of Mitochondrial Respiration

Respiration of the kidney mitochondria was measured as described previously using Fluorescence Lifetime Micro Oxygen Monitoring System (Instech Laboratories, Inc.). The following respiration medium was used (in mM): 125 mM KCl, 10 mM MOPS (pH 7.2), 2 mM $MgCl_2$, 2 mM $KH_2PO_4$, 10 mM NaCl, 1 mM EGTA, 0.7 mM $CaCl_2$, 10 mM glutamate and 2 mM malate. Kidney mitochondria (0.2 mg/ml), ADP (125 μM) and CCCP (0.2 μM) were consequently added to the respiration chamber. Respiratory control ratio was calculated as the rate ratio State 3 to State 4, where State 4 is the rate after ADP phosphorylation.

ATP Levels in Kidney Tissue

ATP concentration in the kidney tissue was measured by luminescent ATP detection assay kit (Abcam; Cat

#ab113849). Luminescence signals were read using a Biotek Synergy H1 plate reader. Luminescence units were calculated as μmol/mg protein based on the ATP calibration curve and protein concentration measured by the Bradford method.

Estimation of Calcium Retention Capacity

Calcium retention capacity (CRC) is the amount of calcium that can be loaded into mitochondria until the permeability transition pore opens. CRC is expressed as nanomol $Ca^{2+}$ per mg of kidney mitochondrial protein. We used the pH method as described previously. This method is based on the fact that in the presence of 1 mM Pi, the $H^+/Ca^{2+}$ ratio is relatively stable, and the pH shift clearly shows the moment when added $Ca^{2+}$ was consumed. Mitochondrial CRC values were estimated in a medium containing 210 mM sucrose, 20 mM KCl, 3 mM glycyl-glycine (pH 7.2), 1 mM $KH_2PO_4$, and 0.5 mg/m mitochondria, final volume 2.0 ml. Substrates were 10 mM glutamate and 2 mM malate. Titration with $CaCl_2$ was performed by addition to mitochondria 5 μl aliquots of 10 mM $CaCl_2$.

Cell Culture

Human aortic endothelial cells (HAEC) were purchased from Lonza (Chicago, IL) and cultured in EGM-2 medium supplemented with 2% FBS but without antibiotics. On the day before the study, the FBS concentration was reduced to 1%.

Superoxide Measurements Using HPLC

Mouse aortic segments were loaded with DHE (50 μM) or mitochondria-targeted mitoSOX (1 μM) in KHB buffer by 30-minute incubation in a tissue culture incubator at 37° C. Next, aortic segments were placed in methanol (300 μl) and homogenized with a glass pestle. The tissue homogenate was passed through a 0.22 μm syringe filter and methanol filtrates were analyzed by HPLC according to previously published protocols. The superoxide specific product 2-hydroxyethidium was detected using a C-18 reverse-phase column (Nucleosil 250 to 4.5 mm) and a mobile phase containing 0.1% trifluoroacetic acid and an acetonitrile gradient (from 37% to 47%) at a flow rate of 0.5 ml/min. 2-Hydroxyethidium was quantified by fluorescence detector using an emission wavelength of 580 nm and an excitation of 480 nm as described previously.

Nitric Oxide Measurements by Electron Spin Resonance (ESR)

Nitric oxide production in aortas was quantified by ESR and colloid $Fe(DETC)_2$ as we have described previously. All ESR samples were placed in quartz Dewar (Corning, New York, NY) filled with liquid nitrogen. ESR spectra were recorded using an EMX ESR spectrometer (Bruker Biospin Corp., Billerica, MA) and a super high Q microwave cavity. The ESR settings were as follows: field sweep, 160 Gauss; microwave frequency, 9.42 GHz; microwave power, 10 milliwatts; modulation amplitude, 3 Gauss; scan time, 150 msec; time constant, 5.2 sec; and receiver gain, 60 dB (n=4 scans).

Vasodilatation Study

Isometric tension studies were performed on 2 mm mouse aortic rings dissected free of perivascular fat from C57B/6J mice. Studies were performed in a horizontal wire myograph (DMT, Aarhus, Denmark, models 610 M and 620 M) containing physiological salt solution with the composition of 130 mM NaCl, 4.7 mM KCl 1.2 mM $MgSO_4$, 1.2 mM $KH_2PO_4$, 15 mM $NaHCO_3$, 5.5 mM glucose, and 1.6 mM $CaCl_2$. The isometric tone of each vessel was recorded using LabChart Pro v7.3.7 (AD Instruments, Australia). The aortic rings were equilibrated over a 2-hour period by heating and stretching the vessels to an optimal baseline tension of 36 mNewtons before contracting them with three cycles of 60 mM KCl physiological saline solution. Endothelial dependent and independent vascular relaxation was tested after pre-constriction with 1 μM phenylephrine. Once the vessels reach a steady state contraction, increasing concentrations of acetylcholine were administered, and the response to each concentration of drug was recorded.

Human Studies

Arterioles (100 to 200-μm diameter) were harvested from human mediastinal fat obtained from patients during cardiac surgery enrolled in the Risk of Oxygen during Cardiac Surgery (ROCS) randomized clinical trial with essential hypertension (BP>140/90 mmHg) and normotensive subjects as previously described for Western blot analysis of SOD2 and SOD2 acetylation. Full informed consent was obtained for all tissue samples.

Statistics

Data are expressed as mean±SEM. To compare the responses to angiotensin II infusion with or without mito2HOBA, two-way analysis of variance (ANOVA) was used followed by a Bonferroni post hoc test. For comparisons between more than two groups, one-way ANOVA followed by a Bonferroni post hoc test was used. For telemetry blood pressure measurements over time, two-way ANOVA with repeated measures was employed using GraphPad Prism 7. P values<0.05 were considered significant.

Results

Figure 8:
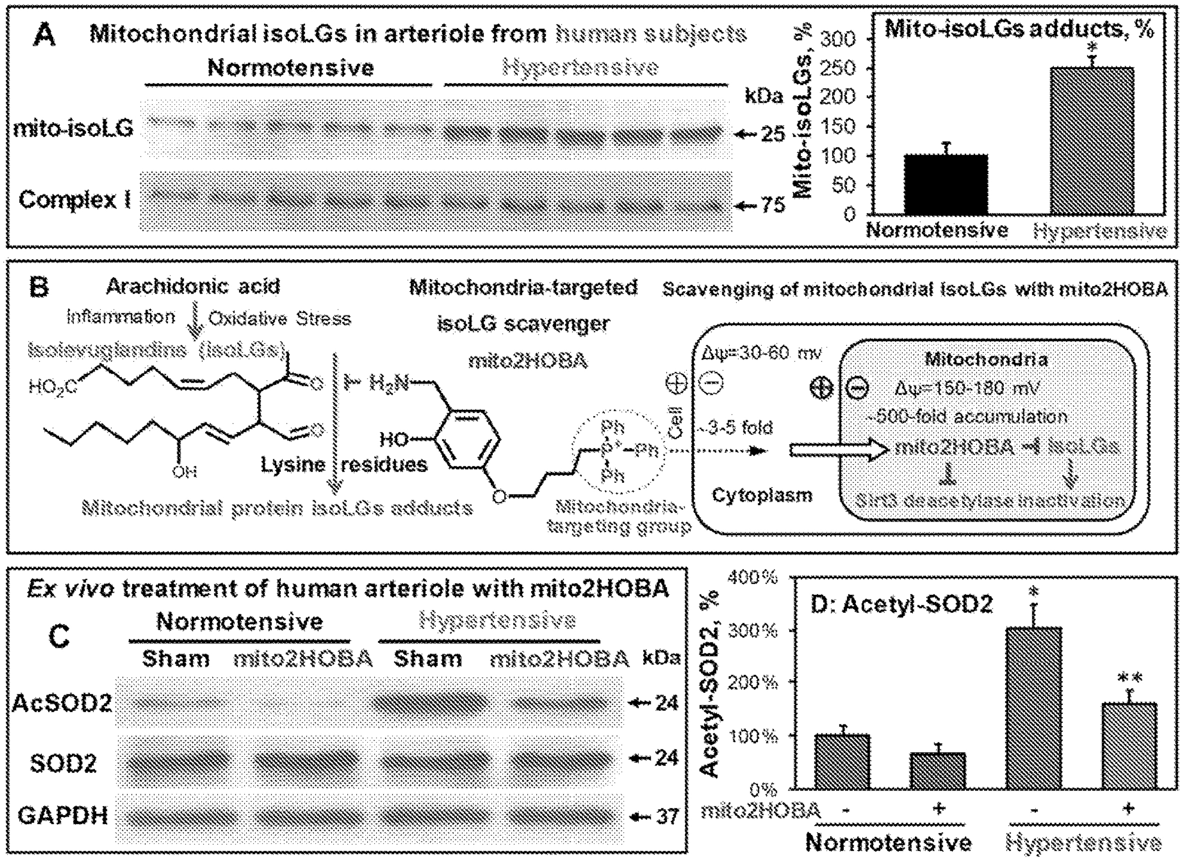
FIGS. 8A-D show Western blots of mitochondrial isoLGs (A) in human arterioles from normotensive and hypertensive subjects (n=5), (B) development of mitochondria-targeted isoLG scavenger mito2HOBA and (C, D) SOD2 acetylation in human arterioles isolated from normotensive and hypertensive subjects and treated ex vivo with mito2HOBA (0.5 μM, 24 hours, DMEM). Data were normalized by Complex I levels (Sham is 100%). Data are mean±SEM. *P<0.01 vs Normotensive Sham, **P<0.01 vs Hypertensive (n=5).

Accumulation of Mitochondrial IsoLGs in Arterioles From Hypertensive Subjects and SOD2 Acetylation Mitochondria are a major source of superoxide radicals and are rich in polyunsaturated fatty acids. Peroxidation of arachidonic acid can produce highly reactive isoLGs which quickly form protein adducts with lysine residues. To test the accumulation of mitochondrial isoLGs, we performed Western blots using the antibody D11, which detects isoLG-adducted proteins independent of the amino acid sequence, in mitochondria isolated from human arterioles. We observed a 250% increase in the mitochondrial isoLG-Lysyl-Lactam protein adducts in mitochondria isolated from hypertensive patients compared with normotensive subjects (FIG. 8A).

Hypertension is associated with inactivation of mitochondrial deacetylase Sirt3 and hyperacetylation of mitochondrial superoxide dismutase (SOD2). To study the potential role of mitochondrial isoLGs in Sirt3 inactivation, we developed the mitochondria-targeted isoLG scavenger mito2HOBA (FIG. 8B). Mito2HOBA selectively accumulates in the mitochondria due to its lipophilic cation triphenylphosphonium. We tested if treatment of human arterioles in organoid cultures with low dose of mito2HOBA stimulates SOD2 deacetylation. Indeed, supplementation with mito2HOBA (0.5 μM 24 hours, DMEM) significantly reduced SOD2 acetylation (FIG. 8C, D). Because SOD2 is deacetylated by Sirt3, these data suggest that mitochondrial isoLGs inhibit Sirt3 function. Moreover, because SOD2 acetylation inactivates SOD2 and contributes to mitochondrial oxidative stress, scavenging mitochondrial isoLGs may reduce mitochondrial oxidative stress.

Figure 9:
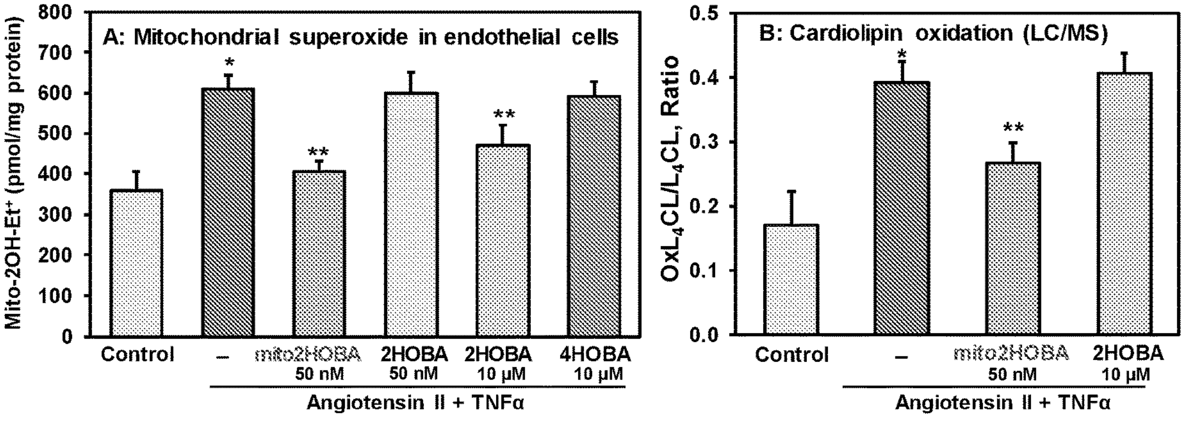
FIGS. 9A and B show the effect of mito2HOBA on mitochondrial superoxide and cardiolipin oxidation in human aortic endothelial cells induced by angiotensin II plus TNFα. (A) Mitochondrial superoxide was measured by HPLC analysis of mitoSOX-superoxide specific product, mito-2-hydroxyethidium (Mito-2OH-Et+). Mito2HOBA (50 nM) abolishes stimulation of mitochondrial superoxide while similar dose of untargeted isoLG scavenger 2HOBA (50 nM) or high dose of isoLG-inactive analog 4HOBA (10 μM) are not protective. *P<0.01 vs control, P<0.001 vs Angiotensin II+TNFα. (B) Cardiolipin oxidation induced by Angiotensin II+TNFα measured my LC/MS. Cardiolipin oxidation is significantly attenuated by mito2HOBA (50 nM) while untargeted 2HOBA (10 μM) is not effective. Supplemental FIG. S1** shows typical chromatograms. Data are mean±SEM. *P<0.01 vs Control, **P<0.01 vs Angiotensin II+TNFα (n=4).

Mitochondria-Targeted IsoLG Scavenger Mito2HOBA Reduces Oxidative Stress in Endothelial Cells The present inventors previously showed that angiotensin II (Ang II) and TNFα promote hypertension and reduce endothelial Sirt3 activity. We tested if mito2HOBA reduces mitochondrial oxidative stress in human aortic endothelial cells (HAEC) stimulated with angiotensin II plus TNFα for 4-hours (FIG. 9). Indeed, supplementation of HAEC with mito2HOBA (50 nM) reduced mitochondrial superoxide production stimulated by TNF□ and Ang II as measured by accumulation of specific superoxide-MitoSOX product, 2-OH-Mito-Ethidium. Importantly, supplementation of cells with an identical concentration of the untargeted isoLG scavenger 2HOBA (50 nM) did not affect mitochondrial superoxide levels. Treatment with isoLGs-inactive analog, 4HOBA, which due to rearrangement of the hydroxyl group site cannot scavenge isoLGs, did not protect endothelial cells from mitochondrial oxidative stress.

Cardiolipin is selectively localized to the matrix side of the mitochondrial inner membrane and cardiolipin oxidation is a specific marker of mitochondrial oxidative stress. We tested if mito2HOBA reduces the cardiolipin oxidation in human aortic endothelial cells stimulated with angiotensin II plus TNFα. Indeed, supplementation of HAEC with low dose of mito2HOBA (50 nM) inhibited cardiolipin oxidation while the untargeted isoLG scavenger 2HOBA was not effective. These data support the role of mitochondrial isoLG in development of mitochondrial oxidative stress associated with SOD2 acetylation.

Figure 10:
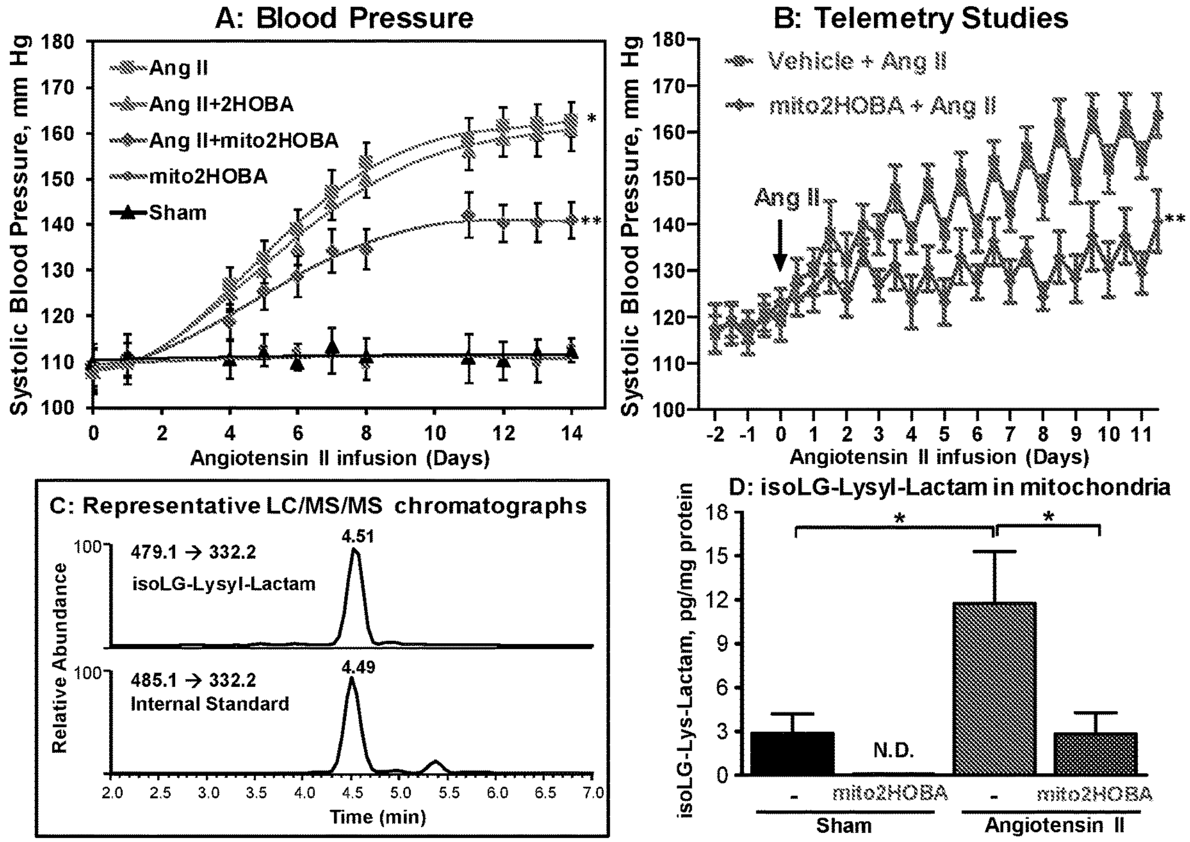
FIGS. 10A-D show the effect of mito2HOBA on angiotensin II-induced hypertension and accumulation of mitochondrial isoLGs protein adducts. (A) Blood pressure tail-cuff measurements in male Sham or angiotensin II-infused mice supplied with mito2HOBA in drinking water (0.1 g/L) or equimolar amount of untargeted analog 2HOBA (0.17 mmol/L). (B) Telemetry studies of blood pressure in angiotensin II-infused mice supplied with mito2HOBA or plain water as a vehicle. (C) Representative LC/MS/MS chromatograms of isoLG-Lysyl-Lactam adduct; (D) isoLG-Lys-Lactam levels in kidney mitochondria isolated from Sham or angiotensin II-infused mice supplied with mito2HOBA. Results are mean±SEM. *P<0.01 vs Sham, **P<0.01 vs Ang II (n=8).

Effects of Mito2HOBA on Mitochondrial IsoLG Protein Adduct Accumulation and Hypertension To test a functional role of mitochondrial isoLGs in hypertension, we used an Ang II model of hypertension, and monitored blood pressure by tail-cuff (FIG. 10A) and telemetry (FIG. 10B). Mito2HOBA alone did not affect the blood pressure in control mice. Infusion of wild-type C57B1/6J mice with Ang II (0.7 mg/kg/day) increased systolic blood pressure to 162 mm Hg. Treatment of mice with mito2HOBA in the drinking water (0.1 g/L) significantly attenuated the Ang II-induced hypertension to 140 mm Hg as measured by both tail-cuff and telemetry. It is important to note that supplementation of mice with the same molar dose of the untargeted analog 2HOBA did not attenuate Ang II-induced hypertension (FIG. 10A).

To provide unambiguous evidence for scavenging of mitochondrial isoLG, we measured isoLG-Lysyl-Lactam adducts accumulation by Liquid Chromatography Tandem Mass Spectrometry (LC/MS) after proteolytic digestion of extracted proteins from isolated mitochondria. Hypertension was associated with 4-fold increase in the mitochondrial isoLG-Lysyl-Lactam protein adducts and mito2HOBA abolished isoLG-Lysyl-Lactam adducts formation in kidney mitochondria (FIG. 10C, D).

Effects of Mito2HOBA on Mitochondrial CypD and SOD2 Deacetylation in Angiotensin 11-Infused Mice In additional experiments, the present inventors discovered that Ang II-induced hypertension is linked to a striking hyperacetylation of mitochondrial proteins (420%) in aortas and that this is normalized by co-treatment of animals with mito2HOBA (FIG. 11A, B). Since Sirt3 is the predominant, if not the only deacetylase in the mitochondria, this suggests that mitochondrial isoLGs reduce activity of Sirt3. Sirt3 activates SOD2 by deacetylation of specific lysine residues and hypertension is linked to SOD2 hyperacetylation. The present inventors tested if scavenging of mitochondrial isoLGs reduces SOD2 acetylation. Indeed, SOD2 acetylation in aortas isolated from hypertensive mice was increased by 260% while mito2HOBA supplementation significantly reduced SOD2 acetylation (147% compared to control mice) (FIG. 11C, D).

The present inventors have reported that deletion of Cyclophilin D (CypD), a regulatory subunit of the mitochondrial permeability transition pore (mPTP), improves vascular function and attenuates hypertension. Sirt3-mediated deacetylation of CypD attenuates mPTP opening. The present inventors sought to determine if Ang II-induced hypertension induces CypD hyperacetylation and if mito2HOBA would attenuate CypD acetylation. Indeed, CypD acetylation was increased by 356% in aortas isolated from hypertensive mice and mito2HOBA supplementation significantly reduced CypD acetylation (156% compared to control) (FIG. 11E).

Figure 11:
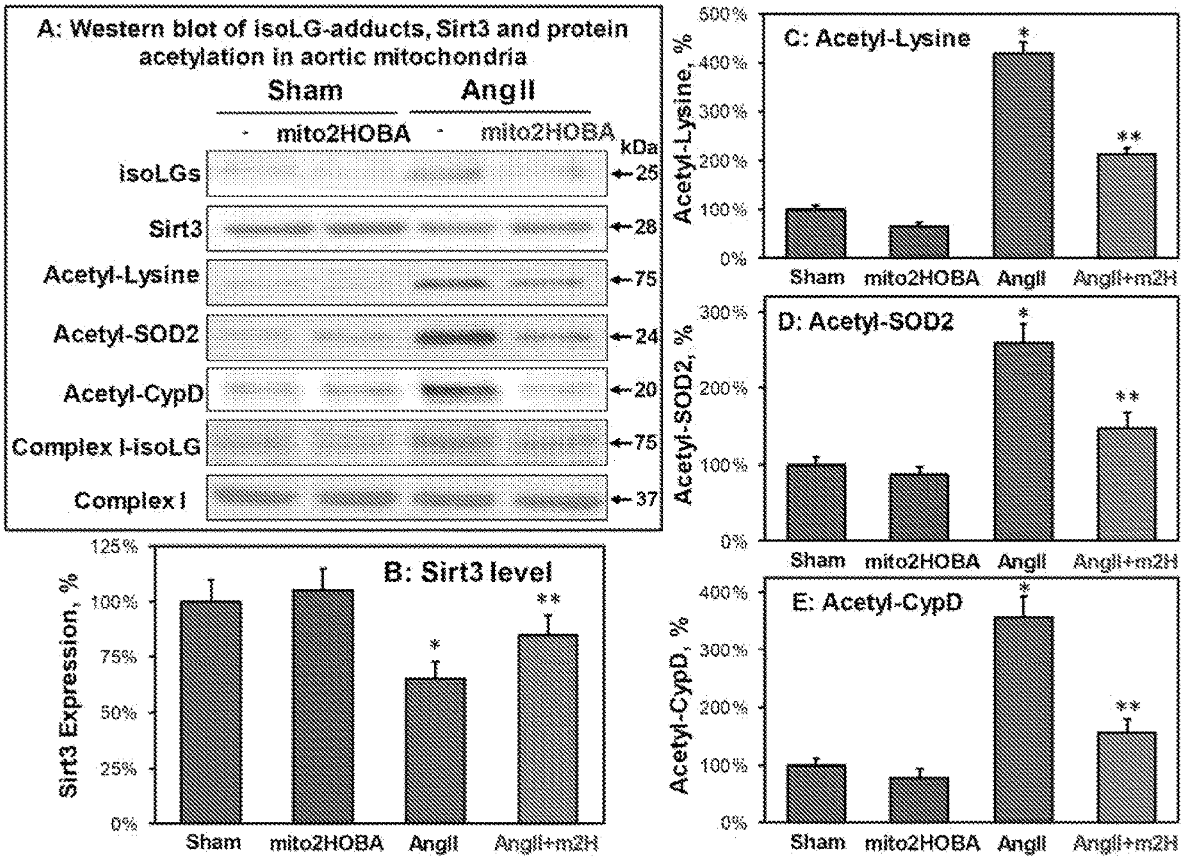
FIGS. 11A-D show Western blot analysis of mitochondrial acetylation in aortas isolated from Sham and angiotensin II-infused mice treated with mito2HOBA. (A) Typical Western blots isoLG-protein adducts (D11 ab), Sirt3, Acetyl-Lysine, SOD2-K68-Acetylation, CypD Acetylation, isoLG adduct with complex I NDUFS1 75 KDa subunit and mitochondrial complex I; (B) Sirt3 levels; (C) mitochondrial protein lysine acetylation; (D) SOD2-K68-Acetyl levels; and (E) CypD-Acetyl levels. Mice supplied with mito2HOBA (m2H) in drinking water (0.1 g/L) and angiotensin II (osmotic pump, 0.7 mg/kg/day) for 14 days. Data were normalized by Complex I levels (Sham is 100%). Results are mean±SEM (n=5). *P<0.01 vs Sham, **P<0.01 vs angiotensin II (Ang II).

Hypertension was associated with accumulation of isoLG-Lysyl-Lactam protein adducts in aortic mitochondria. Mito2HOBA inhibited formation of mitochondrial isoLG adducts and reduced isoLG-complex I NDUFS1 subunit adduct levels which was accompanied with the reduction of mitochondrial acetylation (FIG. 11).

Effect of Mito2HOBA on Aortic Superoxide, Endothelial Nitric Oxide, and Endothelial-Dependent Relaxation Mito2HOBA prevented SOD2 hyperacetylation suggesting that mito2HOBA can reduce mitochondrial superoxide. Indeed, Ang II-infused hypertension was associated with 2-fold increase in aortic mitochondrial superoxide which was completely prevented by mito2HOBA supplementation (FIG. 12A). Hypertension is associated with an increase in vascular superoxide both in the mitochondria and cytoplasm which is facilitated by crosstalk between the mitochondria and the NADPH oxidase. We tested if mito2HOBA reduces cytoplasmic superoxide level in Ang II-infused mice measured by untargeted cellular superoxide probe DHE. Ang II-infused hypertension was associated with 217% increase in aortic cellular superoxide which was substantially reduced by mito2HOBA supplementation (152% compared to Sham control, FIG. 12B).

Figure 12:
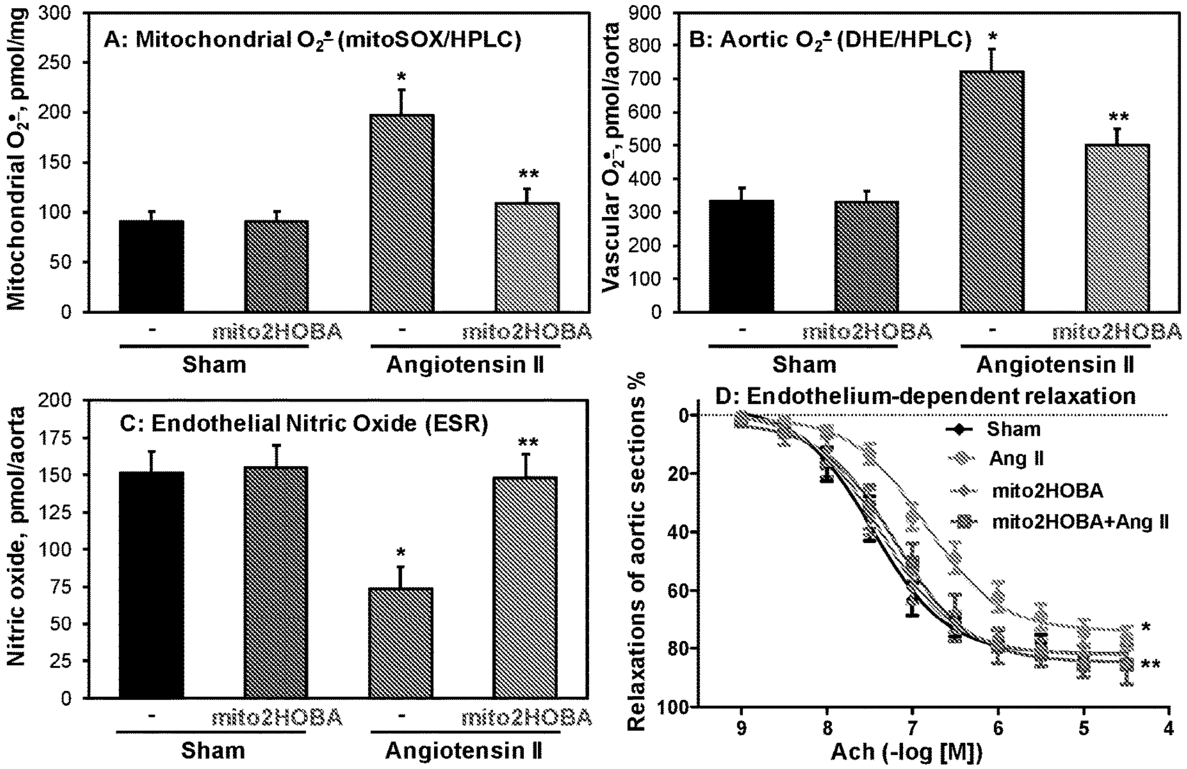
FIGS. 12A-D show the effect of mito2HOBA supplementation on mitochondrial superoxide (A), vascular superoxide (B), endothelial nitric oxide (C) and endothelial-dependent relaxation (D) in angiotensin II-infused mice. Mitochondrial and vascular O2• was measured by mitochondria-targeted superoxide probe mitoSOX (1 μM) or untargeted superoxide probe DHE (50 μM) using HPLC.46 Endothelial nitric oxide was analyzed by NO spin trap Fe(DETC)2 and ESR.47 C57B1/6J mice were infused with Ang II and mito2HOBA was provided in the drinking water (0.1 g/L). Supplemental Figure S2 shows typical HPLC chromatograms. Supplemental figure S3 shows representative ESR spectra of nitric oxide measurements. Results are mean±SEM. *P<0.01 vs Sham, **P<0.01 vs Ang II (n=6).

Increased vascular superoxide contributes to endothelial dysfunction in hypertension. It reduces endothelial nitric oxide levels promoting vasoconstriction and increasing systemic vascular resistance. Decreased nitric oxide bioavailability is therefore a hallmark of endothelial oxidative stress in hypertension. We tested if treatment of mice with mitochondria-targeted isoLG scavenger mito2HOBA protects endothelial nitric oxide and improves endothelial dependent relaxation. Aortic nitric oxide production was quantified by electron spin resonance and specific nitric oxide spin trap $Fe(DETC)_2$. As shown in FIG. 12, Ang II-induced hypertension was associated with 2-fold decrease in endothelial nitric oxide and impaired endothelial-dependent relaxation. Notably, supplementation of mito2HOBA completely prevented the decline in nitric oxide and preserved endothelial-dependent relaxation in Ang II-infused mice (FIG. 12C, D). These data demonstrate a previously unrecognized role of mitochondrial isoLGs in endothelial dysfunction.

Figure 13:
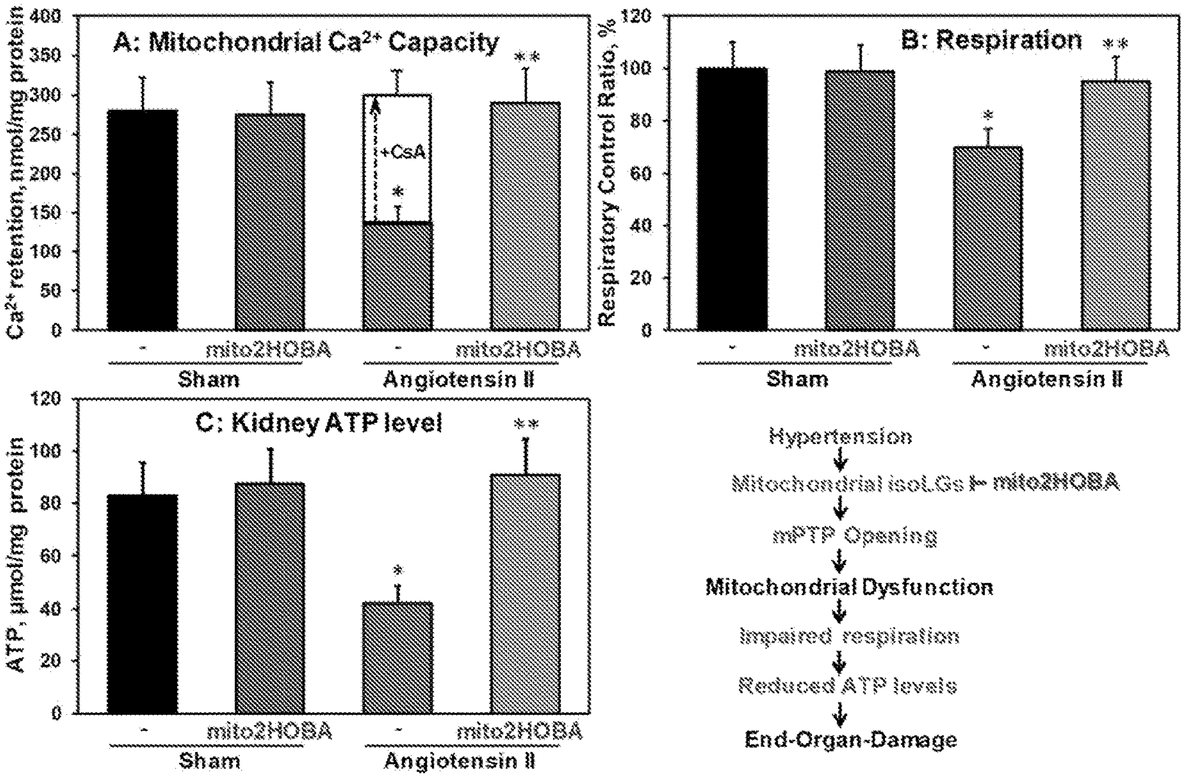
FIGS. 13A-B show mito2HOBA reduces mPTP opening and prevents mitochondrial dysfunc¬tion. C57B1/6J mice were infused with Ang II (0.7 mg/kg/ml) and mito2HOBA in the drinking water (0.1 g/L). Following 14 days of Ang II infusion the animals were sacrificed and kidneys were isolated for mitochondrial studies. Addition of CaCl2 to mitochondria above Ca2+ retention capacity led to mPTP opening and mitochondria swelling. 71 Mitochondria isolated from Ang II-infused mice had significant reduction in Ca2+ capacity due to increased mPTP opening and CypD inhibitor Cyclosporine A (CsA) rescued Ca2+ retention capacity (A). Respiratory control ratio (State 3/State 4) was measured in isolated kidney mitochondria with glutamate and malate (B). Control level is 100%. (C) Renal ATP was measured in freshly isolated tissue by luciferase-based luminescent assay. 72 Results are mean±SEM. *P<0.01 vs Sham, **P<0.01 vs Angiotensin II (n=5).

Effect of Mito2HOBA on Mitochondrial Respiration, Renal ATP Level and $Ca^{2+}$ Retention Capacity Hypertension is associated with mitochondrial dysfunction characterized by impaired respiration and reduced ATP production which can be mediated by mPTP opening and contributes to end-organ damage in hypertension. In the current study, mito2HOBA reduced acetylation of CypD, a $Ca^{2+}$ dependent regulatory subunit of mPTP. We have tested if mito2HOBA supplementation reduces mPTP opening as measured by mitochondrial $Ca^{2+}$ retention capacity, improves mitochondrial respiration and ATP production. Indeed, Ang II-induced hypertension was associated with 50% decrease in renal mitochondrial $Ca^{2+}$-retention capacity and this was normalized by ex vivo supplementation with CypD inhibitor Cyclosporin A. Treatment of Ang II-infused mice with mito2HOBA completely prevented decline in $Ca^{2+}$-retention capacity (FIG. 13A). Furthermore, mito2HOBA also preserved mitochondrial respiration supported by glutamate plus malate as substrates (FIG. 13B).

Ang II-induced hypertension was also associated with a 50% decrease in renal ATP levels and this was prevented by mito2HOBA (FIG. 13C). These data implicate mitochondrial isoLGs in CypD-dependent mPTP opening in hypertension that can inhibit mitochondrial respiration, reduce ATP level, and promote end-organ-damage in hypertension.

Discussion

Figure 14:
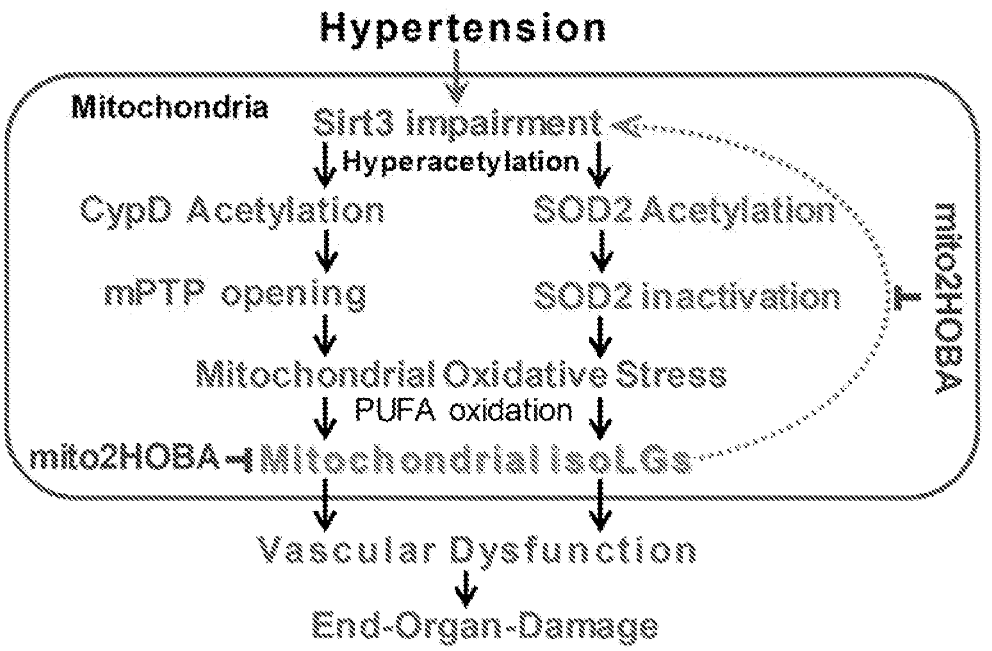
FIG. 14 shows hypertension is linked to Sirt3 inactivation which leads to hyperacetylation of mitochondrial proteins such as cyclophilin D (CypD) and mitochondrial superoxide dismutase (SOD2). CypD acetylation stimulates mPTP opening which increases the production of mitochondrial superoxide while SOD2 acetylation inactivates SOD2. This results in imbalance between the increased superoxide production and diminished superoxide dismutase activity leading to mitochondrial oxidative stress and oxidation of polyunsaturated fatty acids (PUFA) to reactive gamma-ketoaldehydes, isolevuglandins (isoLGs), in the mitochondria. Mitochondrial isoLGs promote vascular and mitochondrial dysfunction while treatment with mitochondria-targeted isoLG scavenger mito2HOBA reduces Sirt3 inactivation, improves mitochondrial and vascular function, and attenuates hypertension. The present invention shows that targeting mitochondrial isoLGs prevents Sirt3 inactivation and can improve the treatment of vascular dysfunction in human subjects.

This example shows the first evidence that mitochondrial isoLGs accumulate in arterioles of patients with essential hypertension and in mice with Ang II-induced hypertension. Mitochondrial isoLGs were significantly increased in mitochondria isolated from arterioles of hypertensive patients compared with normotensive subjects and in mitochondria isolated from aorta and kidney in mice after onset of Ang II-induced hypertension. The formation of mitochondrial isoLG-Lysyl-Lactam protein adducts was confirmed by two independent methods, D11-antibody assay and mass spectroscopy. These methods were previously vigorously validated and provide unambiguous support for accumulation of isoLG-protein adducts in the mitochondria. In addition, the mitochondria-targeted isoLG scavenger mito2HOBA prevented accumulation of isoLG-protein adducts in mitochondria and mito2HOBA increased SOD2 deacetylation in human arterioles from hypertensive patients, reduced mitochondrial superoxide in human aortic endothelial cells, inhibited vascular oxidative stress, improved endothelial function, and reduced Ang II-induced hypertension. Furthermore, mito2HOBA supplementation of Ang II-infused mice raised kidney ATP level, protected mitochondrial respiration, and attenuated mPTP opening, supporting the role of mitochondrial isoLGs accumulation in the development of mitochondrial dysfunction in hypertension. Western blot studies revealed that hypertension was associated with reduced Sirt3 deacetylase activity and mitochondrial hyperacetylation, while mito2HOBA increased Sirt3-mediated deacetylation of mitochondrial proteins, particularly SOD2 and CypD. These findings support the role of mitochondrial isoLGs in SOD2 inactivation and CypD-dependent mPTP opening (see FIG. 14).

Hypertension is a multifactorial disorder associated with mitochondrial oxidative stress; however, the precise targets of mitochondrial oxidative stress in hypertension are not clear. We have previously shown an increased production of mitochondrial superoxide and reduced activity of mitochondrial SOD2 in animal models of hypertension.[12] The imbalance between increased mitochondrial superoxide and reduced SOD2 activity leads to mitochondrial oxidative stress. Mitochondria are the major source of superoxide radicals and they are rich in unsaturated fatty acids such as arachidonic acid. Free radical oxidation of arachidonic acid produces the highly reactive lipid dicarbonyls including isoLGs. They rapidly adduct to protein lysine residues and can induce cellular dysfunction. Our data show a substantial accumulation of isoLG-Lysyl-Lactam protein adducts in mitochondria isolated from vascular and kidney tissue in hypertension. Supplementation with low dose of the mitochondria-targeted isoLG scavenger mito2HOBA (50 nM) prevents mitochondrial oxidative stress in human aortic endothelial cells while untargeted analog 2HOBA is not effective. It is important to note that 2HOBA and mito2HOBA does not react with superoxide, peroxynitrite or hydrogen peroxide and therefore does not exert its effect directly by ROS scavenging. In contrast, the mito2HOBA-mediated reduction in mitochondrial, cellular and aortic superoxide observed in Ang II-infused mice and in HAEC is likely due to enhanced scavenging of this radical by SOD2. This is a reasonable interpretation of our findings because we observed a dramatic reduction in Ang II-induced SOD2 hyperacetylation in mito2HOBA-treated animals and SOD2 is the only mitochondrial superoxide dismutase.

Endothelial dysfunction is linked to increased vascular superoxide which leads to nitric oxide inactivation, reduced endothelial nitric oxide production and impaired endothelial dependent relaxation. Mito2HOBA reduces vascular superoxide, protects endothelial nitric oxide and improves endothelial dependent relaxation. In endothelial cells, mito2HOBA inhibits superoxide production and reduces oxidative stress. These effects of mito2HOBA were associated with increased Sirt3-mediated deacetylation of SOD2 and CypD. Sirt3 impairment contributes to vascular inflammation, hypertrophy and endothelial dysfunction. Our new data support an important role of mitochondrial isoLGs in Sirt3 inactivation, endothelial and vascular dysfunction.

Mitochondrial dysfunction contributes to target-organ-damage in hypertension. Hypertension is a leading cause of kidney disease which is linked to metabolic and mitochondrial dysfunction. In this work, we found that Ang II-induced hypertension is associated with 4-fold increase in renal mitochondrial isoLGs, increased mPTP opening and impaired respiration in kidney mitochondria. These events were associated with a 2-fold decrease in kidney ATP levels. Remarkably, mito2HOBA supplementation prevents accumulation of mitochondrial isoLG in kidney, attenuates mPTP opening, preserves mitochondrial respiration, and protects kidney ATP production. These data strongly support a role of mitochondrial isoLG in hypertensive renal injury. These data are in line with our previous finding showing that mito2HOBA supplementation in lipopolysaccharide treated mice improves respiration of kidney mitochondria and protects the renal cortex from cell injury.

Thus, the present inventors show that Sirt3 inactivation as a new convergent mechanism underling the interplay of major cardiovascular risk factors. Sirt3 impairment inhibits fatty metabolism and inactivates a key mitochondrial antioxidant, superoxide dismutase 2 (SOD2), due to hyperacetylation of specific lysine residues. Therefore, Sirt3 inactivation increases levels of polyunsaturated fatty acids and superoxide which react together producing highly reactive isoLGs in the mitochondria. IsoLGs covalently bind to lysine residues making cytotoxic and pro-inflammatory isoLGs adducts. We discovered 4-fold increase in mitochondrial isoLGs in hypertension. Mitochondrial isoLGs are emerging as a mechanistic link between mitochondrial oxidative stress and disease progression. Previous studies have identified isoLGs adduct with the F1Fo subunit of complex V, and we report formation of isoLG adduct with NDUFS1 subunit of mitochondrial complex I. It is conceivable that mitochondrial isoLGs causes Sirt3 inactivation by direct [64] and indirect interactions. Meanwhile, the cause-and-effect relationship between mitochondrial isoLGs and Sirt3 inactivation remains elusive. It is clear that isoLGs exposure inhibits Sirt3, however, it is also possible that Sirt3 impairment promotes mitochondrial isoLGs formation. Indeed, treatment of human arteriole isolated from hypertensive patients rescues Sirt3 activity and increases Sirt3-mediated SOD2 deacetylation. We show that a feed-forward cycle between Sirt3 inactivation and mitochondrial isoLGs promotes vascular dysfunction and that scavenging mitochondrial isoLGs will break this cycle and improve vascular function (see FIG. 14). Therefore, it appears that isoLGs are both upstream and downstream of Sirt3 inactivation.

Pathophysiological role of isoLGs has been reported in various conditions including vascular inflammation, hypertension, and heart failure. Supplementation with untargeted isoLG scavenger 2HOBA reduces vascular inflammation, diminishes tissue fibrosis, decreases aortic stiffening, abates cardiac hypertrophy, attenuates hypertension and heart failure. In these conditions, stimulation of NADPH oxidases can promote formation of isoLGs in cytoplasm where they can be eliminated by 2HOBA. Meanwhile, mitochondria are both the source and the potential target for isoLGs, therefore, isoLGs produced in the cytoplasm may also contribute to mitochondrial dysfunction. Indeed, our experiments showed that 2HOBA partially attenuates mitochondrial superoxide overproduction in cultured human aortic endothelial cells (FIG. 2) suggesting that both intramitochondrial and extramitochondrial isoLGs promote mitochondrial oxidative stress.

Thus, the present invention shows the effect of mito2HOBA in cultured endothelial cells, in organoid culture with human arterioles and whole animal supplementation. Further studies are needed to determine the specific role of mitochondrial isoLGs in endothelial, smooth muscle, and other cells. We show that compounds of the present invention are effective in blocking of mitochondrial isoLGs will rescue Sirt3 deacetylase activity which recover the metabolic and antioxidant mitochondrial functions reducing vascular oxidative stress and improving the endothelial function, therefore, mito2HOBA can improve the treatment of vascular dysfunction and hypertension.

Hypertension is highly prevalent with aging, and 75% of adults are hypertensive at age of 70 and over. Sirt3 function declines with age and Sirt3 depletion accelerates vascular aging and induces age-dependent hypertension associated with mitochondrial oxidative stress. Sirt3 expression is associated with human longevity and Sirt3 overexpression protects from vascular dysfunction and hypertension. It is intriguing to speculate that Sirt3 impairment and mitochondrial isoLGs can promote age-dependent vascular alterations and hypertension, and scavenging of mitochondrial isoLG, therefore, can slow down and reverse these age-related alterations. Indeed, our human tissue study suggest that mito2HOBA partially rescues Sirt3 activity in the patients with essential hypertension. Of note, most of the oxidants have a very short lifetime (seconds) but isoLGs produce rather stable adducts (lifetime days) which can accumulate with age and, therefore, contribute to the development of age-associated conditions.

In addition to hypertension, mitochondrial oxidative stress likely contributes to many other conditions including aging, atherosclerosis, diabetes, inflammation, and degenerative neurological disorders. Accumulation of mitochondrial isoLGs may impact these conditions. It is conceivable that the use of mitochondria-targeted isoLG scavengers such as mito2HOBA would be beneficial in these conditions. The ability to protect mitochondria in relatively low doses might also limit potential untoward effects compared to untargeted agents such as 2HOBA.

All publications mentioned herein, specifically those mentioned below, are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which need to be independently confirmed.

REFERENCES

[1] W. G. McMaster, A. Kirabo, M. S. Madhur, D. G. Harrison. Inflammation, immunity, and hypertensive end-organ damage. *Circ Res* 116:1022-1033; 2015.

[2] S. S. Davies, V. Amarnath, C. J. Brame, O. Boutaud, L. J. Roberts, 2nd. Measurement of chronic oxidative and inflammatory stress by quantification of isoketal/levuglandin gamma-ketoaldehyde protein adducts using liquid chromatography tandem mass spectrometry. *Nat Protoc* 2:2079-2091; 2007.

[3] C. B. Sullivan, E. Matafonova, L. J. Roberts, 2nd, V. Amarnath, S. S. Davies. Isoketals form cytotoxic phosphatidylethanolamine adducts in cells. *J Lipid Res* 51:999-1009; 2010.

[4] S. S. Davies, L. S. May-Zhang. Isolevuglandins and Cardiovascular Disease. *Prostaglandins Other Lipid Mediat* 139:29-35; 2018.

[5] A. Kirabo, V. Fontana, A. P. de Faria, R. Loperena, C. L. Galindo, J. Wu, A. T. Bikineyeva, S. Dikalov, L. Xiao, W. Chen, M. A. Saleh, D. W. Trott, H. A. Itani, A. Vinh, V. Amarnath, K. Amarnath, T. J. Guzik, K. E. Bernstein, X. Z. Shen, Y. Shyr, S. C. Chen, R. L. Mernaugh, C. L. Laffer, F. Elijovich, S. S. Davies, H. Moreno, M. S. Madhur, J. Roberts, 2nd, D. G. Harrison. DC isoketal-modified proteins activate T cells and promote hypertension. *J Clin Invest* 124:4642-4656; 2014.

[6] I. G. Stavrovskaya, S. V. Baranov, X. Guo, S. S. Davies, L. J. Roberts, 2nd, B. S. Kristal. Reactive gamma-ketoaldehydes formed via the isoprostane pathway disrupt mitochondrial respiration and calcium homeostasis. *Free Radic Biol Med* 49:567-579; 2010.

[7] K. K. Griendling, D. G. Harrison. Out, damned dot: studies of the NADPH oxidase in atherosclerosis. *J Clin Invest* 108:1423-1424; 2001.

[8] W. Han, H. Li, J. Cai, L. A. Gleaves, V. V. Polosukhin, B. H. Segal, F. E. Yull, T. S. Blackwell. NADPH oxidase limits lipopolysaccharide-induced lung inflammation and injury in mice through reduction-oxidation regulation of NF-kappaB activity. *J Immunol* 190:4786-4794; 2013.

[9] K. H. Kim, R. T. Sadikot, L. Xiao, J. W. Christman, M. L. Freeman, J. Y. Chan, Y. K. Oh, T. S. Blackwell, M. Joo. Nrf2 is essential for the expression of lipocalin-prostaglandin D synthase induced by prostaglandin D2. *Free Radic Biol Med* 65:1134-1142; 2013.

[10] A. Panov. Perhydroxyl Radical HO2(*) as Inducer of the Isoprostane Lipid Peroxidation in Mitochondria. *Mol Biol* (*Mosk*) 52:347-359; 2018.

[11] A. Panov, S. Dikalov. Cardiolipin, Perhydroxyl Radicals and Lipid Peroxidation in Mitochondrial Dysfunctions and Aging. *Oxid Med Cell Longev;* 2019.

[12] G. Barja. The mitochondrial free radical theory of aging. *Prog Mol Biol Transl Sci* 127:1-27; 2014.

[13] R. G. Salomon, W. Bi. Isolevuglandin adducts in disease. *Antioxid Redox Signal* 22:1703-1718; 2015.

[14] J. Wu, M. A. Saleh, A. Kirabo, H. A. Itani, K. R. Montaniel, L. Xiao, W. Chen, R. L. Mernaugh, H. Cai, K. E. Bernstein, J. J. Goronzy, C. M. Weyand, J. A. Curci, N. R. Barbaro, H. Moreno, S. S. Davies, L. J. Roberts, 2nd, M. S. Madhur, D. G. Harrison. Immune activation caused by vascular oxidation promotes fibrosis and hypertension. *J Clin Invest* 126:50-67; 2016.

[15] S. Rubattu, B. Pagliaro, G. Pierelli, C. Santolamazza, S. D. Castro, S. Mennuni, M. Volpe. Pathogenesis of target organ damage in hypertension: role of mitochondrial oxidative stress. *Int J Mol Sci* 16:823-839; 2014.

[16] M. P. Murphy, R. A. Smith. Targeting antioxidants to mitochondria by conjugation to lipophilic cations. *Annu Rev Pharmacol Toxicol* 47:629-656; 2007.
[17] I. Lee, M. Huttemann. Energy crisis: the role of oxidative phosphorylation in acute inflammation and sepsis. *Biochim Biophys Acta* 1842:1579-1586; 2014.
[18] D. A. Lowes, N. R. Webster, M. P. Murphy, H. F. Galley. Antioxidants that protect mitochondria reduce interleukin-6 and oxidative stress, improve mitochondrial function, and reduce biochemical markers of organ dysfunction in a rat model of acute sepsis. *Br J Anaesth* 110:472-480; 2013.
[19] A. E. Dikalova, A. K. Pandey, L. Xiao, L. Arslanbaeva, T. Sidorova, M. G. Lopez, F. T. Billings, E. Verdin, J. Auwerx, D. G. Harrison, S. I. Dikalov. Mitochondrial deacetylase Sirt3 reduces vascular dysfunction and hypertension while Sirt3 depletion in essential hypertension is linked to vascular inflammation and oxidative stress. *Circ Res.* 126:439-452; 2020.
[20] A. Dikalova, V. Mayorov, L. Xiao, A. Panov, V. Amarnath, I. Zagol-Ikapitte, A. Vergeade, M. Ao, V. Yermalitsky, R. R. Nazarewicz, O. Boutaud, M. G. Lopez, F. T. IV Billings, S. Davies, L. J. Roberts, D. G. Harrison and S. Dikalov. Mitochondrial Isolevuglandins Contribute to Vascular Oxidative Stress and Mitochondria-Targeted Scavenger of Isolevuglandins Reduces Mitochondrial Dysfunction and Hypertension. Hypertension.76:1980-1991; 2020.

The invention thus being described, it would be obvious that the same can be varied in many ways. Such variations that would be obvious to one of ordinary skill in the art is to be considered as being bard of this disclosure.

Unless otherwise indicated, all numbers expressing quantities of ingredients, properties such as reaction conditions, and so forth used in the Specification are to be understood as being modified in all instances by the term "about." Accordingly, unless indicated by the contrary, the numerical parameters set forth in the Specification and Claims are approximations that may vary depending upon the desired properties sought to be determined by the present invention.

Notwithstanding that the numerical ranges and parameters setting forth the broad scope of the invention are approximations, the numerical values set forth in the experimental sections or the example sections are reported as precisely as possible. Any numerical value, however, inherently contain certain errors necessarily resulting from the standard deviation found in their respective testing measurements.

We claim:

1. A method of treating or ameliorating sepsis in a subject, comprising administering an effective amount of a compound of the following formula:

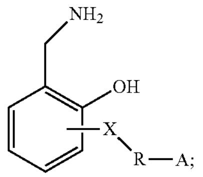

wherein:

X is a bond, alkyl, alkoxy, —O—, or —$CH_2$—;

each R is independent and chosen from $C_1$ to $C_{12}$ substituted or unsubstituted alkyl; and A is

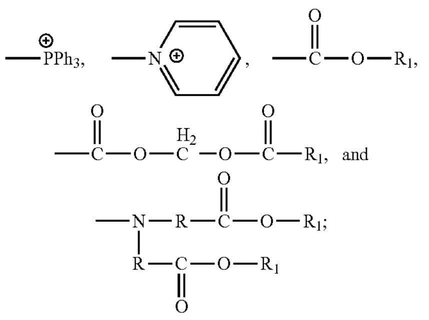

each $R_1$ is independent and chosen from $C_1$ to $C_{12}$ substituted or unsubstituted alkyl; and an optional counterion; and stereoisomers and pharmaceutical salts thereof.

2. The method of claim 1, of the following formula:

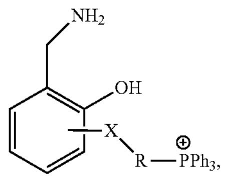

wherein:

X is a bond, alkyl, —O—, or —$CH_2$—; and

R is $C_1$ to $C_{12}$ substituted or unsubstituted alkyl; and stereoisomers and pharmaceutical salts thereof.

3. The method of claim 1, of the following formula:

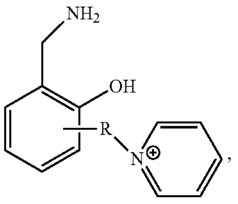

wherein

R is $C_1$ to $C_{12}$ substituted or unsubstituted alkyl; and stereoisomers and pharmaceutical salts thereof.

4. The method of claim 1, of the following formula:

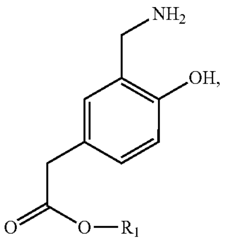

wherein $R_1$ is $C_1$ to $C_{12}$ substituted or unsubstituted alkyl; and stereoisomers and pharmaceutical salts thereof.

5. The method of claim 1, of the following formula:

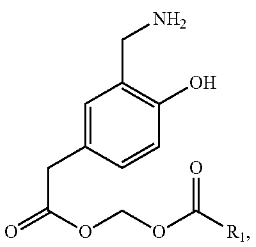

wherein $R_1$ is $C_1$ to $C_{12}$ substituted or unsubstituted alkyl; and stereoisomers and pharmaceutical salts thereof.

6. The method of claim 1, of the following formula:

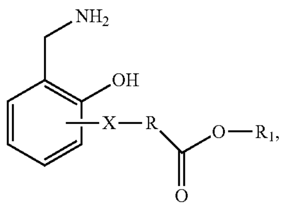

wherein

X is a bond, —O—, or —$CH_2$—;

R is $C_1$ to $C_{12}$ substituted or unsubstituted alkyl; and $R_1$ is $C_1$ to $C_{12}$ substituted or unsubstituted alkyl or acetoxymethyl; and stereoisomers and pharmaceutical salts thereof.

7. The method of claim 1, of the following formula:

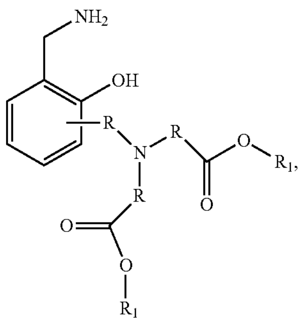

wherein each R is independent and chosen from $C_1$ to $C_{12}$ substituted or unsubstituted alkyl; and each $R_1$ is independent and chosen from $C_1$ to $C_{12}$ substituted or unsubstituted alkyl or acetoxymethyl; and stereoisomers and pharmaceutical salts thereof.

8. The method of claim 1, of the following formula:

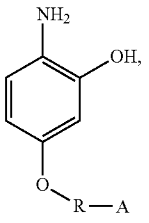

wherein

R is $C_1$ to $C_{12}$ substituted or unsubstituted alkyl; $R_2$ is selected from —P—$Ph_3$; or

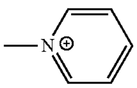;

and stereoisomers and pharmaceutical salts thereof.

9. The method of claim 1, of the following formula:

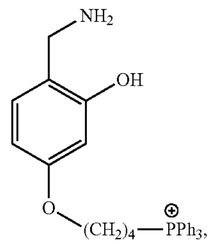

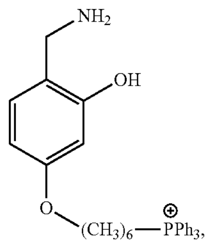

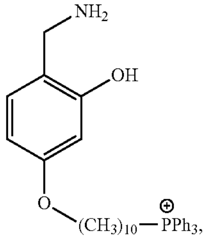

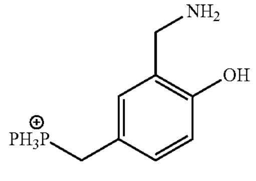

,

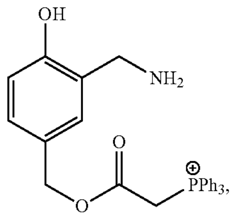

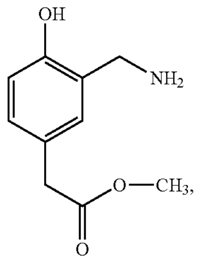

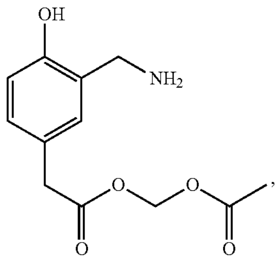

,

-continued
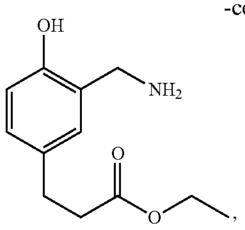
and
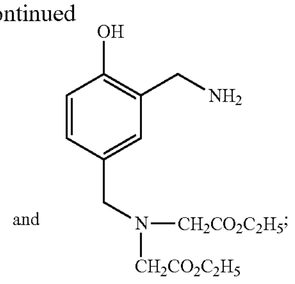
and pharmaceutically acceptable salts thereof.
10. The method of claim 1, of the following formula:
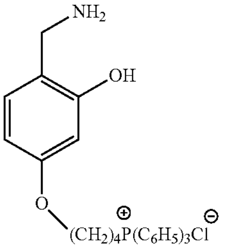
mito2HOBA
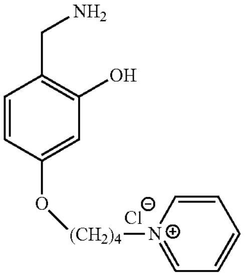
mito2HOBA-4N4
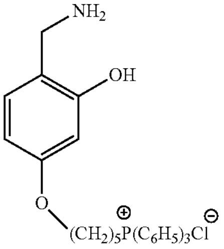
mito2HOBA-C6
-continued
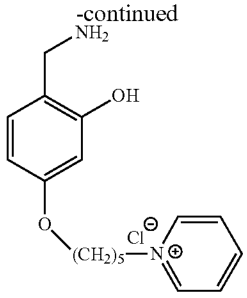
mito2HOBA-4N6
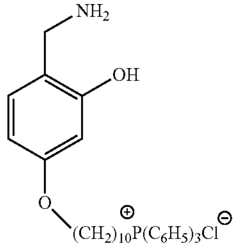
mito2HOBA-C10
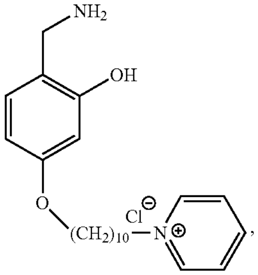
mito2HOBA-4N10
and stereoisomers and pharmaceutical salts thereof.
* * * * *